(12) United States Patent
Miyata et al.

(10) Patent No.: US 10,927,209 B2
(45) Date of Patent: Feb. 23, 2021

(54) POLYURETHANE, URETHANE-(METH)ACRYLIC COMPOSITE RESIN, AND AQUEOUS DISPERSION OF URETHANE-(METH)ACRYLIC COMPOSITE RESIN

(71) Applicant: JAPAN COATING RESIN CORPORATION, Osaka (JP)

(72) Inventors: Shinya Miyata, Osaka (JP); Eri Hatakeyama, Osaka (JP); Ryosuke Kawasaki, Osaka (JP); Aiko Takeda, Osaka (JP)

(73) Assignee: JAPAN COATING RESIN CORPORATION, Osaka (JP)

( * ) Notice: Subject to any disclaimer, the term of this patent is extended or adjusted under 35 U.S.C. 154(b) by 0 days.

(21) Appl. No.: 15/947,043

(22) Filed: Apr. 6, 2018

(65) Prior Publication Data

US 2018/0223027 A1    Aug. 9, 2018

Related U.S. Application Data

(62) Division of application No. 14/910,015, filed as application No. PCT/JP2014/070641 on Aug. 5, 2014, now Pat. No. 9,975,981.

(30) Foreign Application Priority Data

| Aug. 7, 2013 | (JP) | ............... | 2013-163914 |
| Jul. 11, 2014 | (JP) | ............... | 2014-143404 |
| Aug. 5, 2014 | (JP) | ............... | 2014-159605 |
| Aug. 5, 2014 | (JP) | ............... | 2014-159612 |

(51) Int. Cl.

| *C08F 283/00* | (2006.01) |
| *A61K 8/87* | (2006.01) |
| *A61K 8/04* | (2006.01) |
| *A61K 8/06* | (2006.01) |
| *C08G 18/00* | (2006.01) |
| *A61K 8/91* | (2006.01) |
| *A61Q 5/06* | (2006.01) |
| *C08G 18/48* | (2006.01) |
| *C08G 18/34* | (2006.01) |
| *C08G 18/42* | (2006.01) |

(Continued)

(52) U.S. Cl.

CPC ........ *C08F 283/006* (2013.01); *A61K 8/0245* (2013.01); *A61K 8/04* (2013.01); *A61K 8/06* (2013.01); *A61K 8/81* (2013.01); *A61K 8/87* (2013.01); *A61K 8/91* (2013.01); *A61Q 1/00* (2013.01); *A61Q 5/00* (2013.01); *A61Q 5/04* (2013.01); *A61Q 5/06* (2013.01); *A61Q 19/00* (2013.01); *C08G 18/00* (2013.01); *C08G 18/0823* (2013.01); *C08G 18/348* (2013.01); *C08G 18/42* (2013.01); *C08G 18/4202* (2013.01); *C08G 18/4211* (2013.01); *C08G 18/4216* (2013.01); *C08G 18/4238* (2013.01); *C08G 18/4808* (2013.01); *C08G 18/4825* (2013.01); *C08G 18/4833* (2013.01); *C08G 18/4854* (2013.01); *C08G 18/6625* (2013.01); *C08G 18/755* (2013.01); *C08L 51/08* (2013.01); *C09D 151/08* (2013.01); *A61K 2800/10* (2013.01); *A61K 2800/54* (2013.01); *A61K 2800/614* (2013.01); *A61K 2800/654* (2013.01); *C08L 2201/54* (2013.01); *C08L 2207/53* (2013.01)

(58) Field of Classification Search

CPC .............................. A61K 8/87; C08F 283/006

See application file for complete search history.

(56) References Cited

U.S. PATENT DOCUMENTS

| 5,650,159 A | 7/1997 | Lion et al. |
| 2003/0187136 A1 | 10/2003 | Maier et al. |

(Continued)

FOREIGN PATENT DOCUMENTS

| JP | 2587801 | 3/1997 |
| JP | 9-165407 | 6/1997 |

(Continued)

OTHER PUBLICATIONS

International Search Report dated Sep. 2, 2014 in International Application No. PCT/JP2014/070641.

Written Opinion of the International Searching Authority dated Sep. 2, 2014 in International Application No. PCT/JP2014/070641 (with English translation).

Written Opinion of the International Preliminary Examination Authority dated Sep. 15, 2015 in International Application No. PCT/JP2014/070641 (with English translation).

(Continued)

*Primary Examiner* — H. Sarah Park

(74) *Attorney, Agent, or Firm* — Wenderoth, Lind & Ponack, L.L.P.

(57) ABSTRACT

An object of the present invention is to provide an aqueous dispersion for use in a cosmetic, which has both the flexibility and hair styling properties (hair set retention properties), and which allows for easily re-styling hair when the hair style once set has been disturbed; and a cosmetic including the same. In the above mentioned aqueous dispersion and the cosmetic, a polyurethane is used, which is obtainable from a polyol component including at least one type of a polyether polyol and a polyester polyol, and a polyvalent isocyanate component, wherein the polyol component includes: a polyether polyol containing as a major component a structural unit derived from a polyalkylene glycol having from 2 to 4 carbon atoms, and having a number average molecular weight of 400 or more and 4,000 or less; or a polyester polyol containing a structural unit derived from at least one type of dicarboxylic acid selected from the group consisting of phthalic acid, isophthalic acid and terephthalic acid.

22 Claims, 1 Drawing Sheet

(51) Int. Cl.
  *C08G 18/66* (2006.01)
  *C08G 18/75* (2006.01)
  *C08G 18/08* (2006.01)
  *A61Q 1/00* (2006.01)
  *A61Q 5/00* (2006.01)
  *A61K 8/81* (2006.01)
  *A61Q 19/00* (2006.01)
  *A61K 8/02* (2006.01)
  *A61Q 5/04* (2006.01)
  *C08L 51/08* (2006.01)
  *C09D 151/08* (2006.01)

(56) References Cited

U.S. PATENT DOCUMENTS

| | | | |
|---|---|---|---|
| 2010/0297051 | A1 | 12/2010 | Feuillette |
| 2013/0089731 | A1 | 4/2013 | Imanaka et al. |
| 2013/0281636 | A1* | 10/2013 | Hartig ................. C08F 283/006 525/440.08 |

FOREIGN PATENT DOCUMENTS

| | | |
|---|---|---|
| JP | 2004-224868 | 8/2004 |
| JP | 2006-37294 | 2/2006 |
| JP | 2010-53188 | 3/2010 |
| JP | 4491197 | 6/2010 |
| JP | 2010-163612 | 7/2010 |
| JP | 2011-149011 | 8/2011 |
| JP | 2012-67207 | 4/2012 |
| JP | 5281232 | 9/2013 |
| WO | 2012/084668 | 6/2012 |
| WO | WO-2013027093 A1 * | 2/2013 .......... C08F 283/006 |

OTHER PUBLICATIONS

Extended European Search Report dated Nov. 29, 2016 in corresponding European patent application No. 14 833 820.5.
Office Action dated May 22, 2017 in corresponding Chinese Application No. 201480044181.6, with English Translation.
Office Action dated Mar. 6, 2018 in Chinese Patent Application No. 201480044181.6, with partial English-language translation.
Gang Wang et al., "Study on Synthesis of Waterborne Core (PMMA)/Shell (PU) Polyurethane-Acrylate Hybrid Emulsion", Environment-Friendly Paint and Painting Special Issue, obtained from China Academic Journal Electronic Publishing House, 2006, pp. 3-6.
Hongxia Pan et al., "Preparation of Polyurethane Eucalyptus Acrylate Hybrid Emulsion with Core-Shell Structure", Chemical World, Dec. 30, 2005, pp. 57-59, with statement of relevance in attached IDS.
Guo-wen Hu et al., "Preparation and Characterization of Polyurethane Acrylate Hybrid Emulsion", Journal of South China University of Technology (Natural Science Edition), 2007, vol. 35, No. 6, pp. 64-70, with English-language abstract at last page.
Xiaolei Zhu, "Syntheses and Properties of Waterborne Polyurethane/Polyacrylate Core-Shell Emulsions", China Excellence Master's Thesis full text Database Process technology, First Edition, Apr. 15, 2009, pp. 1-59, with English-language abstract at third page.
Takeo Mitsui et al., "New Cosmetology", China Light Industry publishing, 1996, 1st. Edition, No. 398, 5 pages.
Yijun Liu, "Polyurethane Raw Materials and Auxiliaries Handbook", Chemical Industry Publishers, 2005, 1st Edition, pp. 171.

* cited by examiner

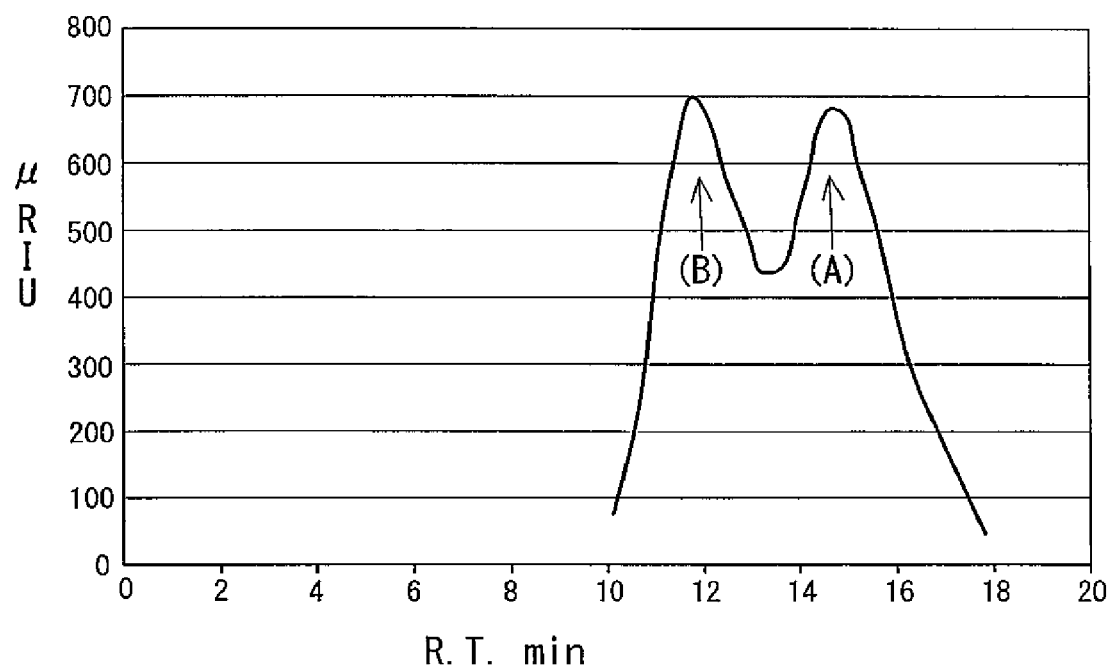

US 10,927,209 B2

POLYURETHANE, URETHANE-(METH)ACRYLIC COMPOSITE RESIN, AND AQUEOUS DISPERSION OF URETHANE-(METH)ACRYLIC COMPOSITE RESIN

TECHNICAL FIELD

The present invention relates to a urethane-(meth)acrylic composite resin, a polyurethane which is a raw material of the urethane-(meth)acrylic composite resin, an aqueous dispersion comprising the urethane-(meth)acrylic composite resin, and a cosmetic including the same. The cosmetic according to the present invention has characteristics that it can be widely applied, for example, in hair cosmetics, make-up cosmetics, skin care cosmetics, eye make-up cosmetics, other cosmetics and the like. Further, the urethane-(meth)acrylic composite resin or the aqueous dispersion thereof according to the present invention can also be suitably used as coatings for industrial or household use, or protective films (coating agents).

BACKGROUND ART

Urethane-(meth)acrylic composite resins are used as cosmetics for retaining hair style, protecting skin or the like, utilizing the film-forming ability thereof (see, the below-identified Patent Documents 1 and 2), or alternatively, as coatings for industrial (for automobiles) or household use, or protective films (see, the below-identified Patent Document 3). However, when a film made of such a resin comes into contact with an oily component, there are cases where the film is dissolved or swollen due to insufficient oil resistance, failing to fully exhibit its performance.

Although an approach such as using a resin having a higher molecular weight or increasing the content of hard segment may be used in order to improve the oil resistance, there are cases where the resulting film may be too hard, thereby reducing the conformability to a base material, and resulting in a peeling when the film is bent, or causing stiffness or discomfort upon use when used as a cosmetic.

As synthetic resins to be used in cosmetics, polymers such as acrylic resins, vinyl acetate resins, vinyl pyrrolidone resins, and vinyl methyl ether resins, of varying ionicity such as anionic, cationic, nonionic or amphoteric ionicity, are widely known. These synthetic resins are used for the purpose of retaining hair style or protecting skin, utilizing their film-forming ability. However, a problem has been pointed out that the resulting film may be too hard or sticky, depending on the resin used.

As a resin for use in a cosmetic in which drawbacks pointed out in the above mentioned resins, such as stiffness or hygroscopicity, are improved, an aqueous dispersion is proposed which contains a urethane-acrylic composite resin composed of composite particles obtained by copolymerization of radical polymerizable monomers in the presence of polymer particles of polyurethane (see the below-identified Patent Documents 1 and 2).

An example of the cosmetics including the resin for use in a cosmetic as described above is a "hair styling agent", which is a hair cosmetic, and it can be prepared in a variety of forms, including an aqueous formulation for use as a mist spray, and a hair wax containing a large amount of an oily component. The resins for use in cosmetics have been widely used not only in hair cosmetics, but also in make-up cosmetic applications, sun care cosmetic applications (such as sunscreens), and skin care cosmetic applications (for protecting skin and providing moisture), for example.

PRIOR ART DOCUMENTS

Patent Documents

Patent Document 1 JP 2587801 B
Patent Document 2 JP 5281232 B
Patent Document 3 JP 2011-149011 A

SUMMARY OF THE INVENTION

Problems to be Solved by the Invention

In cases where the urethane-(meth)acrylic composite resin having the film-forming ability is used in a variety of applications for the purpose of improving the oil resistance, as described above, there has been a problem that, when the composite resin is used in a cosmetic containing a large amount of an oily component, as represented by hair wax among other cosmetics, for example, the ability of the resin to retain hair style or to provide a non-sticky feel in the finished hair may be impaired due to the oily component acting as a plasticizer for the resin, failing to fully exhibit the intrinsic functions of the resin.

Further, as the applications and usages are becoming increasingly diverse, the resins for use in cosmetics are now required to exhibit their functions in a variety of preparations that are more versatile than ever.

Particularly, when used in a cosmetic containing a large amount of an oily component, as represented by the hair wax, there has been a problem that the ability of the resin to retain hair style or to provide a non-sticky feel in the finished hair may be impaired due to the oily component acting as a plasticizer for the resin, failing to fully exhibit the intrinsic functions of the resin.

Accordingly, an object of the present invention is to provide a urethane-(meth)acrylic composite resin capable of retaining its excellent intrinsic properties, without the resulting film being impaired, even when the film comes into contact with an oily component, and an aqueous dispersion thereof; and to provide a specific polyurethane which is used as a raw material of the urethane-(meth)acrylic composite resin; as well as to provide an aqueous dispersion of the urethane-(meth)acrylic composite resin for use in a cosmetic, which has both the flexibility and hair styling properties (hair set retention properties), and which allows for easily re-styling hair when the hair style once set has been disturbed, while retaining a non-sticky feel; and a cosmetic including the same.

Means for Solving the Problems

The first gist of the present invention resides in an aqueous dispersion of an urethane-(meth)acrylic composite resin for use in a cosmetic, characterized in that the aqueous dispersion of the urethane-(meth)acrylic composite resin is obtained by emulsifying and dispersing component (A), which is a polyurethane containing an isocyanate group and a carboxyl group, and component (B), which is a (meth)acrylate-based polymerizable monomer, in an aqueous medium to obtain a pre-emulsion; and by copolymerizing the component (B) in the pre-emulsion; and that the component (A) and the component (B) satisfy the following conditions (1) to (3).

(1) A polyol unit(s) for constituting the component (A) is a polyether polyol.
(2) The polyether polyol comprises as a major component a structural unit derived from a dialkylene glycol having from 2 to 4 carbon atoms, and having a number average molecular weight of 400 or more and 4,000 or less.
(3) The weight ratio of the component (A) to the component (B) ((A)/(B)) is from 80/20 to 30/70.

Another gist of the present invention resides in a cosmetic comprising the above mentioned aqueous dispersion of the urethane-(meth)acrylic composite resin for use in a cosmetic.

The second gist of the present invention resides in a polyurethane obtainable from a polyol component comprising a polyester polyol and a polyvalent isocyanate component; wherein the polyester polyol comprises a structural unit derived from at least one type of dicarboxylic acid selected from the group consisting of phthalic acid, isophthalic acid and terephthalic acid; and wherein film formation by casting of a mixed solution of a silicone oil and the polyurethane (weight ratio 50/50) is possible at 23° C.

Another gist of the present invention resides in a urethane-(meth)acrylic composite resin obtained by complexing the polyurethane and a (meth)acrylic resin, wherein film formation by casting of a mixed solution of a silicone oil and the urethane-(meth)acrylic composite resin prepared at a weight ratio of 50/50, is possible at 23° C.

Still another gist of the present invention resides in an aqueous dispersion of the urethane-(meth)acrylic composite resin obtained by emulsifying and dispersing the urethane-(meth)acrylic composite resin in an aqueous medium; and a cosmetic comprising the urethane-(meth)acrylic composite resin.

Effect of the Invention

In the polyurethane according to the present invention, the easier the film formation of the mixture of the polyurethane and an oily component, the better the oil resistance of the resulting film. This feature is also inherited in the urethane-(meth)acrylic composite resin containing the polyurethane, and the composite resin will exhibit an excellent oil resistance, while retaining its intrinsic properties, such as flexibility, soft touch, and set retention properties.

Further, when the aqueous dispersion according to the present invention is used in a hair cosmetic, the resulting cosmetic is capable of providing a good flexibility and a soft touch to hair, and exhibits good hair set retention properties.

BRIEF DESCRIPTION OF THE DRAWINGS

FIG. 1 is a graph showing the results of the measurement of the weight average molecular weight measured in Example 1-2.

MODE FOR CARRYING OUT THE INVENTION

The present invention will now be described in detail.
In the following, the polyurethane according to the present invention; the urethane-(meth)acrylic composite resin (hereinafter, sometimes abbreviated as U/A resin) according to the present invention, obtainable by using the polyurethane; and the aqueous dispersion of the urethane-(meth) acrylic composite resin (U/A resin) according to the present invention, obtainable by using the U/A resin, will individually be described in detail.

Note that, "(meth)acrylic" as used herein means "acrylic or methacrylic".

<Polyurethane>

The polyurethane according to the present invention is a polyurethane obtainable from a polyol component and a polyvalent isocyanate component, and specifically, a polyurethane obtainable from a polyol component comprising at least one type of a polyether polyol and a polyester polyol, and a polyvalent isocyanate component.

In the following description, the invention which relates to a polyurethane obtainable from a polyol component comprising a polyether polyol, a U/A resin including the polyurethane, and an aqueous dispersion of the U/A resin are each referred to as the "first invention"; and the invention which relates to a polyurethane obtainable from a polyol component comprising a polyester polyol, a U/A resin including the polyurethane, and an aqueous dispersion of the U/A resin are each referred to as the "second invention".

<Polyurethane (Component (A)) According to the First Invention>

The polyether polyol to be used in the polyurethane (component (A)) according to the first invention is characterized in that it is a polyether polyol comprising as a major component a structural unit derived from a polyalkylene glycol having from 2 to 4 carbon atoms, and having a number average molecular weight of 400 or more and 4,000 or less.

The polyurethane, which is the component (A), refers specifically to a polymer containing a carboxyl group, obtained by reacting a polyol unit with a polyvalent isocyanate compound.

The ratio of the used amount of the polyol unit to the polyvalent isocyanate compound, polyol unit:polyvalent isocyanate compound, in terms of equivalence ratio, is preferably from 1:1.2 to 1:2, and more preferably from 1:1.5 to 1:1.9.

The polyol unit refers to a unit composed of an organic compound containing two or more hydroxyl groups within one molecule. Specific examples thereof include: polyols having a relatively low molecular weight, such as ethylene glycol, 1,3-propanediol, 1,3-butanediol, 1,4-butanediol, 1,5-pentanediol, 3-methyl-1,5-pentanediol, 1,6-hexanediol, neopentyl glycol, diethylene glycol, trimethylene glycol, triethylene glycol, tetraethylene glycol, dipropylene glycol, tripropylene glycol, hexandiol, and cyclohexanedimethanol; polyester polyols obtained by polycondensation of at least one type of the above mentioned polyols with at least one type of dicarboxylic acids such as adipic acid, sebacic acid, itaconic acid, maleic anhydride, terephthalic acid, and isophthalic acid; polyether polyols such as polyethylene glycol, polypropylene glycol, polytetramethylene ether polyol, polybutadiene polyol, hydrogenated polybutadiene polyol, and polyalkylene glycols; polycaprolactone polyols, polycarbonate polyols, polyacrylate polyols, and polyether polyols in which propylene oxide is added to the above mentioned polyols; and the like.

Among these, the polyether polyol comprising as a major component a structural unit derived from a polyalkylene glycol as described above is particularly preferred, because it allows for imparting a flexible texture to the resulting polymer.

As the polyol component constituting the polyol unit, one type of polyol unit may be used. However, if at least two types of polyol components each having a different number average molecular weight from each other and/or each comprising a different structural unit are used, the resulting polyol units to be used will be polydisperse polyol units, which exhibit at least two peaks in its molecular weight distribution. The use of such polyol units allow for improving the mechanical strength (elongation, rupture strength) of the resulting polymer, while retaining a flexible texture.

The average number of carbon atoms in the plurality of types of polyol units, which are used as the polydisperse polyol units, is preferably from 2 to 4. If the average number of carbon atoms is within the above mentioned range, a flexible texture can be provided to the resulting polymer.

The average value of the number average molecular weight of the polydisperse polyol units is preferably 300 or more, more preferably 400 or more, still more preferably 500 or more, and particularly preferably 600 or more. Too small a number average molecular weight tends to reduce the flexibility of the resulting polymer. The upper limit of the number average molecular weight, on the other hand, is preferably 4,000, more preferably 3,000, and still more preferably 2,500. Too large a number average molecular weight may result in a reduced self-emulsifiability, or in an excessively increased flexibility depending on the type of the polyol unit used.

As described above, when units derived from a plurality of types of polyols are used, the polyol having the smallest number average molecular weight, of the plurality of types of polyols used, preferably has a number average molecular weight of 400 or more, and more preferably 500 or more. If the polyol has too small a number average molecular weight, the resulting film may be too hard, lacking sufficient flexibility. The upper limit thereof, on the other hand, is preferably 1,200, and more preferably 1,500. If the polyol has too large a number average molecular weight, the self-emulsifiability may be decreased, or the effect of using a low-molecular weight diol may not be sufficiently obtained.

Specific examples of the polyol having the smallest number average molecular weight include: PTMG650 (manufactured by Mitsubishi Chemical Corporation); HIFLEX D1000 (manufactured by DKS Co., Ltd.); Sannix PP1000 (manufactured by Sanyo Chemical Industries, Ltd.); Polyether P-1000 (manufactured by ADEKA Corporation); PEG1000 (manufactured by NOF CORPORATION), and the like.

As described above, when units derived from a plurality of types of polyols are used, the difference between the number average molecular weight of the polyol having the smallest number average molecular weight and the number average molecular weight of the polyol having the largest number average molecular weight, in the plurality of types of polyols used, is preferably 100 or more, and more preferably 500 or more. If the above mentioned difference in the number average molecular weight is too small, the effect of using a plurality of types of polyols may not be sufficiently obtained. The upper limit thereof, on the other hand, is preferably 2,000, and more preferably 1,000. If the above mentioned difference in the number average molecular weight is too large, the total balance of the component (A) may be impaired, resulting in an unstable synthesis reaction.

Further, it is necessary that the component (A) contains a carboxyl group. Further, the acid value of the component (A) is preferably 15 mg KOH/g or more, and more preferably 20 mg KOH/g or more. An acid value of less than 15 mg KOH/g may interfere with the dispersion of the component (A) into water in a subsequent step, possibly resulting in a failure to obtain an aqueous dispersion. The upper limit thereof, on the other hand, is preferably, 60 mg KOH/g, and more preferably 50 mg KOH/g or less. An acid value exceeding 60 mg KOH/g may lead to an insufficient elasticity, or to a reduced adherence to hair when used in a hair styling agent.

Examples of the method for introducing a carboxyl group(s) into the component (A) include a method in which a carboxyl group-containing polyvalent hydroxy compound is used as a part of the polyol unit. Examples of the carboxyl group-containing polyvalent hydroxy compound include a dimethylolalkanoic acid represented by the following Chemical Formula (1), and the like.

In the Formula (1), R represents, for example, an alkyl group having from 1 to 10 carbon atoms, preferably a methyl group or an ethyl group.

Specific examples of the dimethylolalkanoic acid include dimethylolpropionic acid, dimethylolbutanoic acid, and the like. The amount of the carboxyl group-containing polyvalent hydroxy compound used may be adjusted such that the acid value of the component (A) to be produced by polymerization falls within the above mentioned range.

When producing the component (A) by polymerization, the amount of the carboxyl group-containing polyvalent hydroxy compound used, with respect to the total amount of the polyol unit and the carboxyl group-containing polyvalent hydroxy compound, is preferably 30% by mole or more, and more preferably 50% by mole or more. At the same time, the amount thereof is preferably 90% by mole or less, and more preferably 80% by mole or less. By adjusting the amount of the carboxyl group-containing polyvalent hydroxy compound used within this range, the acid value of the component (A) can be adjusted within the above mentioned range.

The polyvalent isocyanate compound used in the production of the polyurethane refers to an organic compound containing at least two isocyanate groups within one molecule, and a polyvalent isocyanate compound such as an aliphatic, alicyclic, and aromatic isocyanate compound can be used. Specific examples of the above mentioned polyvalent isocyanate compound include: dicyclohexylmethane diisocyanate, 1,6-hexamethylene diisocyanate, isophorone diisocyanate, 1,3-cyclohexylene diisocyanate, 1,4-cyclohexylene diisocyanate, 2,4-tolylene diisocyanate, 2,6-tolylene diisocyanate, 4,4'-diphenylmethane diisocyanate, 2,4'-diphenylmethane diisocyanate, 2,2'-diphenylmethane diisocyanate, and the like. Among these, an aliphatic or alicyclic isocyanate is preferred, because the yellowing over time can be reduced.

A urethane-producing reaction for producing the component (A) can be carried out in the absence of a solvent. However, a solvent may be used in order to allow the reaction to proceed uniformly. Examples of the solvent which can be used include: ethers such as dioxane; ketones such as acetone and methyl ethyl ketone; amides such as dimethylformamide, dimethylacetamide, and N-methyl-2-pyrrolidone; and other organic solvents which are inactive to isocyanate groups and have a high affinity with water. It is also possible to use organic solvents other than those mentioned above, which are inactive to isocyanate groups, in other words, which do not contain an active hydrogen group. Further, the component (B) which is inactive to isocyanate groups, in other words, which does not contain an active hydrogen group may be present during the production of the component (A). In this case, the reaction can be carried out more uniformly, due to the reaction system being diluted by the component (B). The reaction to obtain the component (A) is usually carried out at a temperature of about from 50 to 100° C., for a period of time of about from 0.5 to 20 hours. This allows for obtaining the component (A) containing a carboxyl group and having an isocyanate group at its terminal.

As the catalyst to be used in the production of the component (A), any catalyst generally used in a urethanization reaction can be used. Specific examples thereof include dibutyltin dilaurate and the like.

The glass transition temperature (Tg) of the component (A) is preferably −60° C. or more and 250° C. or less. Further, there are cases where the component (A) exhibits multiple glass transition temperatures, which are the glass transition temperature of the soft segment (derived from the polyol unit) of the component (A), and the glass transition temperature of the hard segment (derived from the isocyanate unit) of the component (A). At this time, the glass transition temperature on the lower temperature side (the glass transition temperature of the soft segment) is preferably −60° C. or more, and more preferably −50° C. or more. If the glass transition temperature on the lower temperature side is lower than −60° C., the resulting film may be too flexible. At the same time, the glass transition temperature on the lower temperature side is preferably 0° C. or less, and more preferably −5° C. or less. If the temperature exceeds 0° C., the resulting film tends to have an insufficient flexibility. Further, the glass transition temperature on the higher temperature side (the glass transition temperature of the hard segment) is preferably 30° C. or more, and more preferably 40° C. or more, although it has less effect on the physical properties of the resulting film compared to the glass transition temperature on the lower temperature side. If the glass transition temperature on the higher temperature side is less than 30° C., the resulting film may have a reduced tenacity. The upper limit thereof, on the other hand, is preferably 250° C. or less, and more preferably 200° C. or less. If the temperature exceeds 250° C., the film may be too hard, resulting in a poor texture. The glass transition temperature (Tg) can be measured according to the method specified in JIS K7244-4.

At least one portion of the carboxyl groups contained in the component (A) is preferably neutralized by a basic compound. This allows for improving the dispersibility of the component (A) in an aqueous medium. Examples of the basic compound include organic amine compounds and alkali metal hydroxides. The above mentioned neutralization reaction can be carried out at any time, as long as it is performed during the period after the component (A) is produced and before dispersing the component (A) in an aqueous medium. In the above mentioned period, it is preferred that the reaction be carried out in the first neutralization step to be described later, and as required, in the second neutralization step to be described later.

Preferred examples of the above mentioned organic amine compound include tertiary amine compounds such as trimethylamine, triethylamine, tributylamine, and triethanolamine. Further, examples of the above mentioned alkali metal hydroxides include sodium hydroxide and potassium hydroxide.

The total amount of the above mentioned basic compound used, as the total amount used in the first neutralization step and the second neutralization step to be described later, is preferably 1 equivalent or more, with respect to the amount of carboxyl groups contained in the component (A). In other words, it is preferred that 100% or more of the carboxyl groups in the component (A) be neutralized by the basic compound. If the total amount of the basic compound is less than 1 equivalent, the component (A) may not be well dispersed in the aqueous medium. The upper limit thereof, on the other hand, is preferably 2.0 equivalents, and more preferably 1.5 equivalents. If the total amount exceeds 2.0 equivalents, the basic compound may remain in the emulsion, possibly causing problems when used in a cosmetic.

Examples of the aqueous medium in which the component (A) is dispersed include water; a mixed solution of water and an organic solvent such as methanol or ethanol, which is compatible with water; and the like. Among these, water is preferred, in terms of environmental consideration.

The component (A) can be subjected to a chain extension reaction as required, so that the molecular weight thereof can be adjusted within the preferred range of the peak molecular weight (Mwp) of the urethane component ((A) component) to be describe later. Examples of a chain extender to be used in the chain extension reaction include: compounds containing a plurality of active hydrogens capable of reacting with isocyanate groups; water (including water as the above mentioned aqueous medium); and the like.

Examples of the compound containing a plurality of active hydrogens capable of reacting with isocyanate groups include: polyols and polyamine compounds having from 1 to 8 carbon atoms, and the like. Examples of the polyol include ethylene glycol, diethylene glycol, and the like. Examples of the polyamine compound include diamines such as ethylenediamine, hexamethylenediamine, and isophoronediamine.

When a mixed solution containing the component (A) and the polymerizable monomer (B) is emulsified and dispersed in the aqueous medium to obtain a first emulsion, if water is used as the aqueous medium, there are cases where the chain extension reaction of the component (A) occurs partially due to the water, during the polymerization step of the component (B). In cases where a more active chain extension reaction is intended, after the emulsification and dispersion process to obtain the first emulsion, the above mentioned chain extender can be added thereto to carry out the chain extension reaction. At this time, the chain extension reaction needs to occur at least in one portion of the component (A) contained in the first emulsion. Further, after polymerizing the component (B) contained in the first emulsion or in a second emulsion obtained by allowing the chain extension reaction to occur at least in one portion of the component (A) in the first emulsion, the chain extension of at least one portion of the component (A) in the emulsion may be actively carried out.

<Polyurethane (Component (A2)) According to the Second Invention>

The polyester polyol to be used in the polyurethane (component (A2)) according to the second invention is characterized in that it is a polyester polyol comprising a structural unit derived from at least one type of dicarboxylic acid selected from the group consisting of phthalic acid, isophthalic acid and terephthalic acid.

Further, this polyurethane is characterized in that film formation by casting of a mixed solution of a silicone oil and the polyurethane (weight ratio 50/50), is possible at 23° C.

The polyol component, which is a raw material of the polyurethane according to the present invention, comprises a polyester polyol. The polyester polyol is a compound comprising a structural unit derived from the polyol component (hereinafter, sometimes referred to as a "polyol unit"), and a structural unit derived from a dicarboxylic acid component (hereinafter, sometimes referred to as a "dicarboxylic acid unit").

The polyol unit is a unit composed of an organic compound containing two or more hydroxyl groups within one molecule. Specific examples of the polyol constituting the polyol unit include: diols having a relatively low molecular weight, such as ethylene glycol, propylene glycol, 1,3-propanediol, 1,3-butanediol, 1,4-butanediol, 1,5-pentanediol, 3-methyl-1,5-pentanediol, 1,6-hexanediol, neopentyl glycol, diethylene glycol, trimethylene glycol, triethylene glycol, tetraethylene glycol, dipropylene glycol, tripropylene glycol, and cyclohexanedimethanol; polyester polyols obtained by polycondensation of at least one type of the above mentioned polyols with at least one type of dicarboxylic acids such as adipic acid, sebacic acid, itaconic acid, maleic anhydride, terephthalic acid, and isophthalic acid; polyethylene glycol, polypropylene glycol, polycaprolactone diol, polytetramethylene ether diol, polycarbonate diol, polybutadiene diol, hydrogenated polybutadiene diol, poly(meth)acrylate diols, dialkylene glycols, and polyether polyols in which propylene oxide is added to the above mentioned polyols; and the like.

The dicarboxylic acid unit is a unit composed of an organic compound containing two or more carboxyl groups within one molecule. In the present invention, it is important that a structural unit derived from at least one type of dicarboxylic acid component selected from the group consisting of phthalic acid, isophthalic acid and terephthalic acid (hereinafter, sometimes collectively referred to as a "phthalic acid-based unit") be used as the dicarboxylic acid unit, as described above. By using the above mentioned polyester polyol containing the phthalic acid-based unit, it is possible to impart oil resistance to the resulting polyurethane or urethane-(meth)acrylic composite resin.

Among the polyester polyols containing the phthalic acid-based unit as described above, examples of the polyester polyol containing a structural unit derived from isophthalic acid include: Kuraray Polyol P-1012, 2012, 530, 1030, 2030, and the like (trade names; manufactured by Kuraray Co., Ltd.); Teslac 2474 (trade name; manufactured by Nihon Kasei polymer Co., Ltd); OD-X-2560 (trade name; manufactured by DIC Corporation); HS2F-136P (trade name; manufactured by Hokoku Co., Ltd.); and the like. Examples of the polyester polyol containing a structural unit derived from terephthalic acid include: Kuraray Polyol P-1011, 2011, 2013, 520, 1020, 2020, and the like (trade names; manufactured by Kuraray Co., Ltd.).

Among the polyester polyols containing the phthalic acid-based unit, a polyester polyol containing a structural unit derived from isophthalic acid (hereinafter, sometimes referred to as an "isophthalic acid unit") is preferred.

The content percentage of the dicarboxylic acid unit in the resulting polyurethane is preferably 0.05% by weight or more and 50% by weight or less. If the content percentage of the dicarboxylic acid unit is 0.05% by weight or more, an effect of improving the oil resistance can be obtained. On the other hand, if the content of the dicarboxylic acid unit is 50% by weight or less, it is possible to improve the strength of the resulting film while retaining a sufficient oil resistance. If the content falls outside the above mentioned range, there are cases where the improvement in the oil resistance may be insufficient, or the resulting film may be brittle. The content of the dicarboxylic acid unit is preferably 0.08% by weight or more, and more preferably 0.1% by weight or more. Further, the content is preferably 40% by weight or less, and more preferably, 35% by weight or less. It is necessary that the dicarboxylic acid unit includes a phthalic acid-based unit. Preferably, the dicarboxylic acid unit includes an isophthalic acid unit, in particular. Incorporation of an isophthalic acid unit provides the effect of improving the oil resistance, while retaining the flexibility.

The content of the phthalic acid-based unit (PA unit) ($C_8H_4O_3$=formula weight: 148) in the polyester polyol, or the content of the phthalic acid-based unit in the polyurethane can be calculated as described below. Note that, the polyester polyol is referred to as "PEsPO", the phthalic acid-based unit is referred to as "PA", a diol is referred to as "DOL" (diol unit is referred to as "DOL unit"), and the number of the phthalic acid-based unit is referred to as "NumberPA".

In the polyester polyol, (both) terminals are diol terminals at all times, therefore, the following relation is satisfied.

Number of phthalic acid – based unit ($PA$ unit) in the polyester ($PEsPO$) =

(molecular weight of $PEsPO$ – molecular weight of terminal $DOL$)/

($PA$ unit formula weight + $DOL$ unit formula weight) = $NumberPA$ (In the above formula, "PA unit formula weight+DOL unit formula weight" is the formula weight of an ester unit in PEsPO composed of a PA unit and a DOL unit)

PA unit content percentage in PEsPO (wtPA (weight fraction))=(NumberPA×PA unit formula weight)/molecular weight of PEsPO (2)

PA unit content (weight) in the charged amount of PEsPO (F)=F×wtPA (3)

PA unit content (% by weight) in polyurethane=(F× wtPA)×100/total amount of polyurethane(=total charged amount of raw materials of urethane) (4)

In cases where a dicarboxylic acid other than the phthalic acid-based unit is used in combination as the acid component, the formula weight of the other dicarboxylic acid (—OC—X—CO—O—, wherein "X" is a divalent hydrocarbon group other than benzene ring) used in combination and the formula weight of PA unit, each multiplied by each of the molar fraction thereof, are added to obtain the "average formula weight of dicarboxylic acids", and this average formula weight is used instead of the "PA unit formula weight" described in 1) in the above calculation to obtain the "total number of dicarboxylic acid units", which corresponds to the above mentioned "NumberPA". Using the thus obtained values, the "dicarboxylic acid unit content (% by weight) in polyurethane" can be calculated in the same manner as described above, and the thus obtained amount is divided proportionally based on the molar fraction and the formula weight of both the units to obtain the "PA unit content in polyurethane".

When a plurality of types of diol components are used, the calculation can be carried out in the same manner.

In cases where a commercially available product or the like whose composition is not clear is used, a composition analysis can be carried out using a method capable of analyzing a polymeric substance, such as nuclear magnetic resonance spectroscopy (NMR) or gel permeation chromatography (GPC), to obtain the composition thereof.

As the polyol component of the polyurethane according to the present invention, a component comprising a polyol and a monocarboxylic acid can also be preferably used in addition to the above mentioned polyol components.

As the above mentioned component, a dimethylolalkanoic acid such as dimethylolpropionic acid, and dimethylolbutanoic acid, or a sulfonic acid-containing polyol is preferably used, and dimethylolalkanoic acid is particularly preferably used. In addition, various types of polyalkylene glycols, polyester polyols, polycarbonate polyols and the like, other than those mentioned above can also be used as the polyol component, as long as the effect of the present invention is not impaired.

These dimethylolalkanoic acids have a structure as shown in the above mentioned Chemical Formula (1).

In the Formula (1), R is an alkyl group having from 1 to 10 carbon atoms, for example, and preferably an alkyl group having from 1 to 6 carbon atoms. Particularly preferred are those in which R is a methyl group or an ethyl group. Among others, one in which R is a methyl group is preferred, in other words, the dimethylolalkanoic acid is preferably dimethylolpropionic acid.

The use of a dimethylolalkanoic acid as described above, allows for obtaining a good copolymerizability, introducing carboxyl groups into the resulting polyurethane thereby improving the dispersion stability when used as an aqueous dispersion, as well as imparting reactivity to the resulting polyurethane. In addition, when used in a cosmetic, in particular, it allows for improving the miscibility with a polar component, and improving the adherence to hair and skin.

The amount of the dimethylolalkanoic acid used may be adjusted as appropriate, depending on the intended acid value of the polyurethane to be obtained, or the performances (such as dispersibility into water) required for the finally resulting urethane-(meth)acrylic composite resin (U/A resin).

As the above mentioned polyol component, one type of polyol component may be used, or components derived from a plurality of types of polyols may be used.

As the polyol component constituting the polyol unit, one type of polyol unit may be used. However, if at least two types of polyol components each having a different number average molecular weight from each other and/or each comprising a different structural unit are used, the resulting polyol units to be used will be polydisperse polyol units, which exhibit at least two peaks in its molecular weight distribution. The use of such polyol units allow for improving the mechanical strength (elongation, rupture strength) of the resulting polymer, while retaining a flexible texture.

The average number of carbon atoms in the plurality of types of polyol units, which are used as the polydisperse polyol units, is preferably from 2 to 4. If the average number of carbon atoms is within the above mentioned range, a flexible texture can be provided to the resulting polymer.

The average value of the number average molecular weight of the polydisperse polyol units is preferably 300 or more, more preferably 400 or more, still more preferably 500 or more, and particularly preferably 600 or more. Too small a number average molecular weight tends to reduce the flexibility of the resulting polymer. The upper limit of the number average molecular weight, on the other hand, is preferably 4,000, more preferably 3,000, and still more preferably 2,500. Too large a number average molecular weight may result in a reduced self-emulsifiability, or in an excessively increased flexibility depending on the type of the polyol unit used.

As described above, when units derived from a plurality of types of polyols are used, the polyol having the smallest number average molecular weight, of the plurality of types of polyols used, preferably has a number average molecular weight of 400 or more, and more preferably 500 or more. If the polyol has too small a number average molecular weight, the resulting film may be too hard, lacking sufficient flexibility. The upper limit thereof, on the other hand, is preferably 1,200, and more preferably 1,500. If the polyol has too large a number average molecular weight, the self-emulsifiability may be decreased, or the effect of using a low-molecular weight diol may not be sufficiently obtained.

As described above, when units derived from a plurality of types of polyols are used, the difference between the number average molecular weight of the polyol having the smallest number average molecular weight and the number average molecular weight of the polyol having the largest number average molecular weight, in the plurality of types of polyols used, is preferably 100 or more, and more preferably 500 or more. If the above mentioned difference in the number average molecular weight is too small, the effect of using a plurality of types of polyols may not be sufficiently obtained. The upper limit thereof, on the other hand, is preferably 2,000, and more preferably 1,000. If the above mentioned difference in the number average molecular weight is too large, the total balance of the component (A) may be impaired, resulting in an unstable synthesis reaction.

As the polyvalent isocyanate used for the production of the polyurethane, the above mentioned polyvalent isocyanate can be used.

The resulting polyurethane contains acid components derived from the above mentioned diol component, particularly a polyester polyol, and a dimethylolalkanoic acid or the like. The acid value of the polyurethane is preferably 15 mg KOH/g or more, and more preferably, 20 mg KOH/g or more. An acid value of less than 15 mg KOH/g may result in a poor dispersibility into water, and in an extreme case, a failure to obtain an aqueous dispersion. The upper limit thereof, on the other hand, is preferably, 60 mg KOH/g, and more preferably, 50 mg KOH/g or less. If the acid value exceeds 60 mg KOH/g, the resulting polymer may have an insufficient elasticity, or may be too hard, causing stiffness or producing white powder during use when used as a hair cosmetic, and thereby being inappropriate for use as a cosmetic.

The acid value can be measured according to the potentiometric titration method (JIS-K-0070) in which potassium hydroxide is used. Note that, in the measurement, the "amount of polyurethane" is used as the mass of the sample.

Further, in cases where potassium hydroxide is used for the neutralization in the production of the polyurethane, for example, salt exchange is less likely to occur, and accordingly, there are cases where the measurement according to the above mentioned method specified in JIS may be difficult. In this case, the "theoretical acid value" corresponding to 1 g of polyurethane can be calculated according to the following equation, to be used as the acid value.

Theoretical acid value (mg KOH/g–polyurethane)
=number of moles of acid-containing raw materials charged×56.1 (molecular weight of KOH)/ amount of polyurethane (g)×1,000

The conditions for carrying out the polyurethane-producing reaction for producing the component (A1), such as the solvent to be used, presence of the component (B), reaction temperature, reaction time, catalyst, chain extension reaction and the like, may be the same as the conditions used in the polyurethane-producing reaction for producing the component (A).

In the production of the polyurethane according to the present invention, the ratio of the amount used of the polyester polyol to the polyvalent isocyanate compound, polyester polyol:polyvalent isocyanate compound, as the equivalence ratio of the hydroxyl groups in the polyester polyol to the isocyanate groups in the polyvalent isocyanate compound, is preferably from 1:1.2 to 1:2, and more preferably from 1:1.5 to 1:1.9.

The weight average molecular weight of the above mentioned polyurethane is preferably 1,000 or more, and more preferably 2,000 or more. A weight average molecular weight of less than 1,000 may increase the hardness of the resulting film, possibly causing a feeling of stiffness when used as a cosmetic. The upper limit of the weight average molecular weight, on the other hand, is usually about 150,000, preferably, 100,000, and more preferably, 70,000. A weight average molecular weight of greater than 150,000 may increase the viscosity of the prepolymer itself, leading to gelation or a failure to obtain a stable emulsion.

The component (A1) may have the same glass transition temperature(s) (Tg) as the glass transition temperature(s) (Tg) of the above mentioned component (A), for the same reasons.

In the above mentioned polyurethane, at least one portion of the carboxyl groups contained therein is preferably neutralized by one type or two or more types of basic compounds. This allows for improving the dispersibility of the polyurethane in an aqueous medium. Examples of the basic compound include organic amine compounds and alkali metal hydroxides. The neutralization reaction can be carried out at any time, as long as it is performed after the production of the polyurethane, and it may be carried out as a single step, or may be divided into two or more steps. Further, a different type of basic compound may be used in each of the neutralization reaction steps.

However, it is preferred that the neutralization step be divided into two steps, and that the first neutralization step be carried out after the production of the polyurethane, and the second neutralization step be carried out after dispersing the polyurethane which has been neutralized in the first step in an aqueous medium.

Examples of the organic amine compound, which can be preferably used, include tertiary amine compounds such as trimethylamine, triethylamine, tributylamine, and triethanolamine. Examples of the alkali metal hydroxide include sodium hydroxide, and potassium hydroxide.

The total amount of the basic compound(s) used (as the total amount used in the first neutralization step and the second neutralization step) is preferably 1 equivalent or more with respect to the amount of carboxyl groups contained in the polyurethane. In other words, it is preferred that 100% or more of the carboxyl groups in the polyurethane be neutralized by the basic compound. If the total amount of the basic compound is less than 1 equivalent, the polyurethane may not be well dispersed in the aqueous medium. The upper limit thereof, on the other hand, is preferably 2.0 equivalents, and more preferably 1.5 equivalents. If the total amount exceeds 2.0 equivalents, the basic compound may remain in the emulsion, possibly causing problems when used in a cosmetic.

Examples of the aqueous medium in which the polyurethane is dispersed include: water; a mixed solution of water and an organic solvent such as methanol or ethanol, which is compatible with water; and the like. Among these, water is preferred, in terms of environmental consideration.

With this polyurethane, film formation by casting of a mixed solution of a silicone oil and the polyurethane prepared at a weight ratio of 50/50, is possible at 23° C. The expression that "film formation by casting is possible" means that, after a film has been formed by casting and allowed to stand at 23° C. for 6 hours, when a portion of the film is picked up by forceps or the like, the entire film can be lifted up without the film being ruptured. Examples of the silicone oil which can be used in the film formation by casting include cyclopentasiloxane (for example, KF-995 (volatile cyclic silicone; manufactured by Shin-Etsu Chemical Co., Ltd.)), and the like.

Due to the characteristics that film formation by casting of a mixed solution of the silicone oil and the polyurethane prepared at a weight ratio of 50/50 is possible at 23° C., the polyurethane exhibits an excellent film-forming ability when used in a cosmetic (cosmetic preparation) containing a large amount of an oily component, such as mascara, lipstick, lip cream, or hair wax. This allows for providing an effect of improving the make-up retention (long-lastingness) or imparting firmness due to the coating effect, when used as a cosmetic.

<U/a Resin and Aqueous Dispersion of U/a Resin According to the First Invention>

The U/A resin according to the first invention of the present invention, in which the above mentioned component (A) and a (meth)acrylate-based polymerizable monomer (B) (hereinafter referred to as "component (B)") are complexed, can be obtained by copolymerizing the polyurethane and the (meth)acrylic resin.

In order to produce the above mentioned U/A resin, for example, a method can be used in which an emulsion is prepared by emulsifying and dispersing the component (A) and component (B) in an aqueous medium, and then the component (B) is subjected to emulsion polymerization in the emulsion. At this time, the U/A resin is obtained as an aqueous dispersion of the U/A resin.

Examples of the (meth)acrylate-based polymerizable monomer, which is the component (B), include alkyl (meth)acrylates and the like. Specific examples thereof include: methyl (meth)acrylate, ethyl (meth)acrylate, propyl (meth)acrylate, isopropyl (meth)acrylate, butyl (meth)acrylate, isobutyl (meth)acrylate, s-butyl (meth)acrylate, t-butyl (meth)acrylate, pentyl (meth)acrylate, s-pentyl (meth)acrylate, 1-ethylpropyl (meth)acrylate, 2-methylbutyl (meth) acrylate, isopentyl (meth)acrylate, t-pentyl (meth)acrylate, 3-methylbutyl (meth)acrylate, neopentyl (meth)acrylate, hexyl (meth)acrylate, 2-methylpentyl (meth)acrylate, 4-methylpentyl (meth)acrylate, 2-ethylbutyl (meth)acrylate, cyclopentyl (meth)acrylate, cyclohexyl (meth)acrylate, heptyl (meth)acrylate, 2-heptyl (meth)acrylate, 3-heptyl (meth) acrylate, octyl (meth)acrylate, 2-octyl (meth)acrylate, 2-ethylhexyl (meth)acrylate, isooctyl (meth)acrylate, nonyl (meth)acrylate, 3,3,5-trimethylhexyl (meth)acrylate, decyl (meth)acrylate, undecyl (meth)acrylate, lauryl (meth)acrylate, cetyl (meth)acrylate, stearyl (meth)acrylate, eicosyl (meth)acrylate, docooyl (meth)acrylate, tetracocyl (meth) acrylate, methylcyclohexyl (meth)acrylate, isobornyl (meth) acrylate, norbornyl (meth)acrylate, benzyl (meth)acrylate, phenethyl (meth)acrylate, and the like. Among these, an alkyl (meth)acrylate in which the alkyl group has from 1 to 24 carbon atoms is preferred, and one in which the alkyl group has from 1 to 8 carbon atoms is particularly preferred.

One type of the component (B) may be used alone, or a plurality of types may be used as a mixture.

In addition to the component (B), other monomer(s) other than the (meth)acrylic monomer, such as an ester group-containing vinyl monomer, a styrene derivative, a vinyl ether-based monomer and/or the like may be used in combination as necessary, to the extent that the object and the effect of the present invention are not impaired. Examples of the ester group-containing vinyl monomer include hydrophobic vinyl monomers such as vinyl acetate, diethyl maleate, and dibutyl maleate; unsaturated group-containing macromonomers such as radical polymerizable unsaturated group-containing silicon macromonomers, and the like.

Further, examples of the styrene derivative include styrene, α-methylstyrene, p-methylstyrene, vinyltoluene, and the like. Specific examples of the vinyl ether-based monomer include vinyl methyl ether, vinyl cyclohexyl ether, and the like.

The glass transition temperature (Tg) of the homopolymer or copolymer composed of the component (B), in other words, the glass transition temperature of the homopolymer when one type of monomer is used as the component (B), or the glass transition temperature of the copolymer, based on the composition ratio thereof, when a plurality of types of monomers are used as the component (B), is preferably 0° C. or more, more preferably 5° C. or more, still more preferably 40° C. or more, and particularly preferably 60° C. or more. If the glass transition temperature is lower than 0° C., the thermal reversibility (including the setting properties) of the resulting cosmetic may be deteriorated. At the same time, the glass transition temperature is preferably 120° C. or less, and more preferably 110° C. or less. A glass transition temperature exceeding 120° C. leads to an increased minimum film forming temperature, possibly resulting in a failure to obtain a uniform film. By controlling the glass transition temperature to be within the above mentioned range, the plasticization of the polymer due to oil can be inhibited even in a cosmetic having a high oil content.

The glass transition temperature (Tg) can be measured according to the JIS method as described above in the section of the component (A), or alternatively, it can be calculated based on the following equation (1) (FOX equation):

$$1/Tg = (Wa/Tga) + (Wb/Tgb) + (Wc/Tgc) + \ldots \quad (1)$$

wherein Tg represents the glass transition temperature (K) of (co)polymer; each of Tga, Tgb, Tgc and the like represents the glass transition temperature (K) of the homopolymer of each of the constituent monomers a, b, c and the like; and each of Wa, Wb, We and the like represents the weight fraction of each of the constituent monomers a, b, and c in the copolymer.

In cases where the Tg needs to be expressed in "° C.", it can be calculated by subtracting "273" from the numerical value of the Tg obtained by the above equation.

In cases where a mixture of a plurality of (meth)acrylate-based polymerizable monomers is used as the component (B), it is preferred that the mixture contain a first monomer whose homopolymer has a high Tg and a second monomer whose homopolymer has a low Tg. By using the plurality of monomers whose homopolymers have different Tgs as the component (B), as described above, the flexibility of the resulting film can be adjusted to a suitably level.

The Tg of the homopolymer of the first monomer is preferably 95° C. or more, and more preferably 100° C. or more. If the Tg of the first monomer is lower than 95° C., the adjustable range of the film flexibility is reduced. The upper limit thereof is usually about 150° C.

Further, the Tg of the homopolymer of the second monomer is preferably 30° C. or less, and more preferably 10° C. or less. If the Tg of the second monomer is greater than 30° C., the resulting film may have an insufficient flexibility, or the adjustable range of the film flexibility may be reduced. The lower limit thereof, on the other hand, is preferably −70° C., and more preferably −60° C. If the Tg is lower than −70° C., there are cases where the resulting film may be sticky.

Next, the method for producing an aqueous dispersion of the U/A resin for use in a cosmetic according to the present invention will be described. As described above, the aqueous dispersion of the U/A resin for use in a cosmetic according to the present invention is obtained as follows: the component (A) and the component (B) are mixed to prepare a mixed solution, and the mixed solution is then emulsified and dispersed in an aqueous medium to obtain an emulsion, followed by polymerization of the component (B) in the emulsion, thereby obtaining an aqueous emulsion of an urethane-(meth)acrylic composite resin. Further, the chain extension reaction of the component (A) is carried out as necessary, during the above mentioned process.

The mixed solution containing the component (A) and the component (B) can be prepared by any method, as long as the component (A), which is made water dispersible by neutralizing at least one portion of the carboxyl groups contained therein, and the component (B) can be uniformly dispersed in an aqueous medium, and the timing at which the component (B) is added is not particularly limited.

Examples of the method therefor include one in which the component (B) is added before neutralizing at least one portion of the carboxyl groups in the component (A); and one in which the component (B) is added after the neutralization. It is also possible to mix one portion or the entire amount of the component (B) with the polyol unit, the polyvalent isocyanate compound and the like, which are raw materials of the component (A), and to allow the reaction of the polyol unit, the polyvalent isocyanate compound, the carboxyl group-containing polyvalent hydroxy compound and the like in the presence of the component (B), thereby producing the component (A). In cases where the remaining amount of the component (B) is added after the production of the component (A), the remaining component (B) may be added at any time before, at the time of, or after the neutralization of the carboxyl groups in the component (A).

Of the above mentioned methods, the method is preferred in which the polyol unit, the carboxyl group-containing polyvalent hydroxy compound and the polyvalent isocyanate are allowed to react in the presence of the component (B) to obtain the component (A) is preferred, because the component (A) and the component (B) can be more uniformly mixed (hereinafter, this step is referred to as a "pre-polymerization step").

Examples of the method for allowing the polyol unit, the carboxyl group-containing polyvalent hydroxy compound and the polyvalent isocyanate to react include a method in which polymerization is carried out in the presence of a urethane polymerization catalyst, such as dibutyltin dilaurate.

The mixing ratio of the component (A) to the component (B) in the above mentioned mixed solution, (A)/(B), in a weight ratio in terms of pure content is preferably from 80/20 to 30/70, and more preferably from 70/30 to 35/65. If the content of the component (A) exceeds 80% by weight, the thermal reversibility (including the setting properties) when used as a hair styling agent may be deteriorated. On the other hand, if the content is less than 20% by weight, it may result in an insufficient emulsification during the synthesis, occurrence of gelation when dispersed into water, or a failure to obtain a uniform aqueous dispersion.

The concentration of the component (A) and the component (B) in the mixed solution is not particularly limited. However, it is preferred that the concentration be adjusted such that the content of a non-volatile component(s) in the finally resulting aqueous emulsion composition is 20% by weight or more, and more preferably 30% by weight or more. If the content of the non-volatile component is less than 20% by weight, a longer time may be required for drying. The upper limit thereof, on the other hand, is preferably 70% by weight or less, and more preferably 60% by weight or less. If the content of the non-volatile component exceeds 70%, there are cases where the adjustment of the water dispersibility may be difficult, or the dispersion stability may be reduced.

In cases where none of the carboxyl groups in the component (A) has been neutralized, it is preferred to add the basic compound to the mixed solution of the component (A) and the component (B) to neutralize at least one portion of the carboxyl groups contained in the component (A), thereby obtaining the neutralized product of the component (A) (hereinafter, this step is referred to as a "first neutralization step").

The amount of the carboxyl groups to be neutralized in the first neutralization step is preferably 0.5 equivalents or more with respect to the total amount of the carboxyl groups in the component (A), and more preferably 0.55 equivalents or more.

If the amount of the carboxyl groups neutralized in the first neutralization is equal to or more than 1 equivalent, the second neutralization step to be described later need not be carried out. If the neutralized amount is less than 1 equivalent, on the other hand, the second neutralization step to be described later is carried out as required.

Next, the mixed solution of the neutralized product of the component (A) and the component (B) is emulsified and dispersed in the aqueous medium (hereinafter, this step is referred to as an "emulsification step"). The method for adding the aqueous medium to the mixed solution of the neutralized product of the component (A) and the component (B) is not particularly limited, and examples of the method therefor include one in which the aqueous medium is dropped into the mixed solution to be dispersed, and one in which the mixed solution is dropped into the aqueous medium to be dispersed.

The temperature at which the mixed solution is emulsified and dispersed in the aqueous medium is preferably 0° C. or more, and more preferably 10° C. or more. At the same time, the temperature is preferably 80° C. or less, and more preferably 60° C. or less. If the temperature is too high, there is a potential risk that the component (A) may be denatured.

In the thus obtained emulsified dispersion, the component (B) is subjected to polymerization to obtain an aqueous emulsion of a urethane-(meth)acrylic composite resin (hereinafter, this step is referred to as a "polymerization step"). The polymerization reaction of the component (B) can be carried out using a common polymerization method appropriate for the component (B) to be used, for example, by adding a radical polymerization initiator to the mixed solution.

As the radical polymerization initiator, a conventional radical polymerization initiator can be used. Examples thereof include: azo initiators such as azobisisobutyronitrile, azobis-2,4-dimethylvaleronitrile, and azobiscyanovaleric acid; persulfate initiators such as sodium persulfate, potassium persulfate, and ammonium persulfate; and organic peroxide initiators such as t-butyl hydroperoxide, dilauroyl peroxide, t-butyl peroxy-2-ethylhexanoate, and t-butyl peroxypivalate. Further, a redox polymerization initiator, which is a combination of an organic peroxide initiator or a persulfate initiator with a reducing agent such as ascorbic acid, Rongalite or a metal sulfite is also preferably used. The amount of the radical polymerization initiator to be used, with respect to the amount of the polymerizable monomer (B), is preferably about from 0.1 to 5% by weight, and more preferably about from 0.5 to 2% by weight.

The polymerization of the component (B) is preferably carried out at a polymerization temperature of from 10 to 80° C., and more preferably from 30 to 60° C. By maintaining the temperature at about 40 to 90° C. for about 30 minutes to 3 hours after the generation of exothermic heat has completed, the polymerization will largely be completed. Thus, the aqueous emulsion of the urethane-(meth)acrylic composite resin is obtained.

Examples of the diols having a relatively high molecular weight described in the above mentioned (1) include polyester diols obtained by condensation polymerization of a diol having a low molecular weight and a dicarboxylic acid; and diols having a molecular weight (weight average) of 1,000 or more, such as polyalkylene glycols.

Specific examples of the diols having a low molecular weight include diols having a molecular weight of less than 500, such as ethylene glycol and propylene glycol. Specific examples of the polyalkylene glycols include polyethylene glycol, polypropylene glycol, polytetramethylene ether glycol, (hydrogenated) polybutadiene diol, and the like. In addition, a polycaprolactone diol, a polycarbonate diol, a polyacrylate diol, and the like can also be used.

Usually, unreacted component (B) remains in the aqueous emulsion of the urethane-(meth)acrylic composite resin obtained in the above mentioned polymerization step. In order to prevent the odor resulting therefrom, the concentration of the remaining component (B) is preferably reduced, for example, to 100 ppm or less, and more preferably to 70 ppm or less. The closer to 0, the more preferred.

Examples of the method for reducing the concentration of the component (B) include a method in which the aqueous emulsion is heated to allow the remaining component (B) to volatilize; a method in which a gas such as air is allowed to pass through the gas phase portion of the emulsion; a method in which water vapor is blown into the emulsion; and a method in which the component (B) is distilled under reduced pressure. These methods may be carried out in combination as required (hereinafter, this step is referred to as a "deodorization step").

In cases where the aqueous emulsion is heated, the liquid temperature of the aqueous emulsion is preferably 40° C. or more, and more preferably, 60° C. or more. At the same time, the liquid temperature is preferably equal to or lower than the boiling point of the aqueous medium, and more preferably 100° C. or less. In cases where a gas is blown into or passed through the emulsion, the temperature of the gas is preferably 20° C. or more and 100° C. or less, and more preferably, 60° C. or more and 95° C. or less. Also in cases where water vapor is blown into the emulsion, it is preferred that the liquid temperature of the aqueous emulsion satisfy the above mentioned conditions.

In cases where a gas is passed through the emulsion, the amount of gas passed therethrough (volume/time, under the conditions in which the gas is used) is preferably from 2 to 100 times by volume (with respect to the volume of the gas phase portion in a container)/min, and more preferably, from 5 to 80 times by volume/min, but not particularly limited thereto. If the amount of gas passed through the emulsion is less than 2 times by volume/min, the removal of the component (B) tends to be insufficient. If the amount thereof is greater than 100 times by volume/min, there are cases where accretions may be formed on the wall of the container due to the scattering of the aqueous emulsion or the formation of a film on the liquid surface, and thus it is not preferred.

The moisture evaporated due to the heating as described above may be supplemented as required after the removal of the component (B). Since it is not desirable to release the exhaust air containing the component (B) into the air, it is preferred to cool the exhaust air to obtain a concentrated liquid, and then the liquid is collected into a tank or the like, to be subjected to a waste water treatment.

The thus obtained aqueous dispersion of the urethane-(meth)acrylic composite resin in which the residual amount of the component (B) is reduced to 100 ppm or less can be used in a cosmetic, such as a hair styling agent, as a virtually odorless raw material. Further, the use of the aqueous dispersion of the urethane-(meth)acrylic composite resin according to the present invention allows for providing a hair styling agent which has a good thermal reversibility (including setting properties) and which gives hair a good texture and smoothness.

At any one point between the above mentioned emulsification step and the polymerization step as well as between the polymerization step and the deodorization step, at least one portion of the component (A) (including the neutralized product of the component (A); the same applies hereinafter) may be subjected to chain extension, as required. Alternatively, one portion of the component (A) may be subjected to chain extension between the emulsification step and the polymerization step, and in addition, at least one portion of the component (A) whose polymer chains have been left unextend in the above mentioned chain extension step may be subjected to chain extension between the polymerization step and the deodorization step.

Since water, which is the dispersion medium, also causes the chain extension reaction of the component (A) to occur gradually in the emulsion, there are cases where the chain extension reaction occurs partially during the polymerization step. However, since the chain extension due to water usually proceeds at a slow rate, it is preferred to use a chain extender other than the above mentioned water, to actively carry out the chain extension reaction, so that the chain extension can be carried out more effectively and reliably. This allows for obtaining a urethane polymer whose chains have been extended more swiftly, and which is capable of forming a flexible and elastic film.

In addition, at any one point selected from: between the emulsification step and the polymerization step; between the polymerization step and the deodorization step; and after the deodorization step, at least one portion of the carboxyl groups in the component (A) may further be neutralized using the basic compound (hereinafter, this step is referred to as a "second neutralization step"). By adjusting the degree of neutralization to a predetermined level, it is possible to obtain an effect of improving the storage stability and the film-forming ability of the resulting emulsion, and the like.

The total amount of the basic compound to be used in the first neutralization step and in the second neutralization step, with respect to the amount of the carboxyl groups in the component (A), is preferably 1 equivalent or more. In cases where 1 equivalent or more of the basic compound has already been used in the first neutralization step, the second neutralization step may be omitted.

The basic compound to be used in the first neutralization step and the second neutralization step is preferably used as an aqueous solution or an aqueous dispersion, so that it can be easily added and mixed. The urethane-(meth)acrylic composite resin which has been neutralized is dissolved or dispersed in water alone, in a mixed solvent of a polar organic solvent and water, or in an organic solvent. Examples of the organic solvent include alcohols, ketones, and other organic solvents. Examples of the alcohols include alcohols having from 1 to 8 carbon atoms, such as ethanol, propanol isopropanol, butanol, benzyl alcohol, and phenyl ethyl alcohol; and alcohols having a valence of two or more, such as glycerin, and alkylene glycols, for example, ethylene glycol and propylene glycol. Examples of the ketones include acetone, methyl ethyl ketone, and the like. Examples of the other organic solvents include low-boiling-point hydrocarbons such as pentane; ethers such as dimethyl ether, and dimethoxymethane; glycol ethers such as mono-, di-, and tri-ethylene glycol monoalkyl ether; and esters such as methyl acetate.

The weight average molecular weight (Mw) of the urethane-(meth)acrylic composite resin (U/A composite resin), in the aqueous dispersion of the U/A composite resin obtained in the present invention, is preferably 180,000 or more, and more preferably 200,000 or more. Too low a weight average molecular weight (Mw) may result in a poor pigment dispersibility. The upper limit of the weight average molecular weight (Mw), on the other hand, is preferably, 1,000,000, and more preferably 800,000. Too high a weight average molecular weight (Mw) may result in a poor smoothness when coated on hair. By adjusting the weight average molecular weight (Mw) within the above mentioned range, it is possible to obtain a particularly excellent oil resistance (film formability by casting of a mixed solution of a silicone oil and the U/A composite resin).

The ratio (Mw/Mn) of the weight average molecular weight (Mw) to the number average molecular weight (Mn) of the U/A composite resin in the aqueous dispersion of the U/A composite resin, is preferably 10 or more, and more preferably, 20 or more. If the ratio Mw/Mn is too low, it tends to be difficult to provide both the flexibility and a high hair setting ability (high C. R. value) at the same time. The upper limit of the ratio Mw/Mn, on the other hand, is preferably 70, and more preferably 60. If the ratio Mw/Mn is too high, the texture of the resulting film may be deteriorated, due to either or both of the polymer having a lower molecular weight and the polymer having a higher molecular weight.

Further, the most frequently observed molecular weight, of the weight average molecular weights (Mw) of the urethane component contained in the U/A composite resin, in other words, in a chart (chromatogram) obtained by measuring the Mw of the U/A composite resin by gel permeation chromatography method (GPC method), as shown in FIG. 1, the molecular weight at the position of the peak (the portion of the graph shown in FIG. 1 as (A)) which corresponds to the polymer of the urethane component (hereinafter, the most frequently observed molecular weight of the polymer of the urethane component is referred to as the peak molecular weight (Mwp) of the polymer of the urethane component, and sometimes referred to as the "Mwp of the urethane component") is preferably 10,000 or more, and more preferably 20,000 or more. If the Mwp of the urethane component is lower than 10,000, the long term stability of the U/A resin may be insufficient, and in an environment where the temperature rises above 30° C., for example, there is a potential risk that the degradation of the U/A resin may be accelerated. The upper limit of the Mwp of the urethane component, on the other hand, is preferably 200,000, and more preferably 100,000. If the Mwp of the urethane component is greater than 200,000, there are cases where the U/A resin may be too hard, resulting in a poor texture, or the viscosity of the system may be increased excessively during the synthesizing step, resulting in a poor productivity.

In addition, the peak molecular weight (Mwp) of the polymer of the acrylic component (the portion of the graph shown in FIG. 1 as (B), hereinafter, sometimes referred to as the "Mwp of the acrylic component) contained in the U/A composite resin is preferably 200,000 or more, and more preferably 250,000 or more. If the Mwp of the acrylic component is lower than 200,000, the 1,3BG resistance and/or the pigment dispersibility of the U/A resin may be deteriorated. The upper limit of the Mwp of the acrylic component, on the other hand, is preferably 2,000,000, and more preferably, 1,500,000. If the Mwp of the acrylic component is higher than 2,000,000, the resulting resin may have a poor texture.

Further, the difference between the peak molecular weight (Mwp) of the acrylic component and the peak molecular weight (Mwp) of the urethane component ((Mwp of acrylic component)–(Mwp of urethane component)) contained in the U/A composite resin is preferably 200,000 or more, and more preferably, 250,000 or more. If the above mentioned difference is less than 200,000, the smoothness when coated on hair and the 1,3BG resistance may not be obtained at the same time. The upper limit of the difference, on the other hand, is preferably 2,000,000, and more preferably, 1,000,000. If the difference is greater than 2,000,000, the smoothness when coated on hair and the 1,3BG resistance may not be obtained at the same time, due to the difference being too large.

The "1,3BG resistance" generally means that, when 1,3BG (1,3-butanediol) is added to the aqueous dispersion, no change occurs in the sample liquid, and is one of the properties to be tested in a blending stability test. Particularly, in a cosmetic application, the "1,3BG resistance" means that there is no difference in the results in the C. R. test to be described later, regardless of the presence or absence of 1,3BG, in other words, the resin to be measured is not affected by 1,3BG.

When the (meth)acrylate-based polymerizable monomer, which is the component (B), is subjected to emulsion polymerization in an aqueous medium, a chain transfer reaction to the polymerization initiator, emulsifying agent and/or the like, and/or to the other polymers generated, in the aqueous medium, is likely to occur during the polymerization, and there are cases where the molecular weight of the resulting polymer is reduced.

However, since in the present invention, a pre-emulsion is prepared by emulsifying and dispersing the component (A) (polyurethane containing an isocyanate group and a carboxyl group) and the component (B) ((meth)acrylate-based polymerizable monomer) in an aqueous medium, and the component (B) is polymerized in the pre-emulsion to produce the aqueous dispersion of the urethane-(meth)acrylic composite resin (U/A resin aqueous dispersion), the radical polymerization occurs in the situation where the component (B) being present inside the component (A) within emulsion droplets. At this time, since the component (B) is protected by the component (A), the chain transfer reaction is less likely to occur in the component (B) during the polymerization. In addition, since the polymerization is allowed to proceed under the conditions where a polymerization termination reaction is less likely to occur, the molecular weight of the component (B) tends to be increased. Thus, a composite resin having a core-shell structure, in which the urethane resin forms a shell portion and the (meth)acrylic resin forms a core portion, is obtained. The molecular weight of the component (B) at this time tends to be higher as compared to the molecular weight thereof when subjected to emulsion polymerization in the absence of the component (A), and the molecular weight distribution of the resulting composite resin will exhibit two peaks, as shown in FIG. 1. Not that, the horizontal axis ($RT_{min}$) in the graph shown in FIG. 1 represents the retention time (min), and it is shown that the shorter the RT, the higher the molecular weight.

The molecular weight distribution of the above mentioned composite resin is as shown in FIG. 1, and the position of each of the peaks, in other words, the relationship between the Mwp of the acrylic component and the Mwp of the urethane component is as described above.

In cases where it is difficult to clearly discriminate the peak molecular weight (Mwp) of the urethane component from the peak molecular weight (Mwp) of the acrylic component contained in the U/A composite resin, in other words, when two peaks are not clearly observed in the chart (chromatogram) of the U/A composite resin obtained by gel permeation chromatography method (GPC method), as shown in FIG. 1, the urethane component and the acrylic component may be separately subjected to polymerization under the corresponding conditions to obtain respective aqueous dispersions, followed by measuring the Mw of the respective components by gel permeation chromatography method (GPC method) to obtain chromatograms, and the molecular weight at the position of the peak in each of the chromatograms may be defined as the peak molecular weight (Mwp) of the urethane component or the peak molecular weight (Mwp) of the acrylic component. It should be noted, however, the measured value of the Mwp of the acrylic component (component (B)), in particular, will usually be lower than the actual value, in this case, because the above described effect of increasing the molecular weight is not provided.

The minimum film forming temperature (MFT) of the aqueous dispersion of the U/A composite resin obtained in the present invention, as measured according to JIS K6828-2 to be described later, is preferably −10° C. or more, and more preferably −5° C. or more. If the MFT is lower than −10° C., the resulting film may be too soft, leading to insufficient setting properties or thermal reversibility. The upper limit of the MFT, on the other hand, is preferably 60° C., more preferably 50° C., still more preferably 30° C., and further still more preferably 20° C. If the MFT is higher than 60° C., there are cases where the resulting film may be too hard, and at the same time, the film formation may be difficult under the living environment, making the aqueous dispersion unsuitable for a cosmetic application and the like.

In the present invention, a variety of methods are used in order to adjust the minimum film forming temperature of the urethane-(meth)acrylic composite resin within the above mentioned suitable range. As the methods for lowering the minimum film forming temperature, for example, the following methods (1) to (3) can be mentioned. It should be noted that the opposite approaches to the following methods can be taken in order to raise the minimum film forming temperature.

(1) As the polyol unit, the amount to be used of a diol(s) having a relatively high molecular weight, for example, a molecular weight exceeding 1,000, is increased.
(2) The equivalence ratio of the polyol unit to the polyvalent isocyanate compound used in the production of the component (A) is adjusted so as to be close to 1:1.
(3) As the component (B), one/those having a low glass transition temperature (Tg) is/are used.

The gel fraction of the aqueous dispersion of the U/A composite resin obtained in the present invention is preferably 50% by weight or more, and more preferably 60% by weight or more. A gel fraction of less than 50% by weight tends to result in an insufficient hardness, a poor blending stability, or a poor dispersion stability. The upper limit of the gel fraction, on the other hand, is preferably 99% by weight, and more preferably 95%. A gel fraction of greater than 99% by weight may result in an excessive hardness, or cause stiffness when used in a cosmetic application. By adjusting the gel fraction within the above range, the above mentioned oil resistance (film formability by casting) is further improved. This property can be obtained particularly effectively, by adjusting the weight average molecular weight (Mw) of the U/A resin within the above mentioned range.

<U/A Resin and Aqueous Dispersion of U/A Resin According to the Second Invention>

(1) Production Method of Urethane-(Meth)Acrylic Composite Resin (U/A Resin)

The U/A resin in which a polyurethane and a (meth) acrylic resin are complexed can be obtained by polymerizing the component (B) in the presence of the above mentioned (A1) component.

The U/A resin as described above can be produced using a method, for example, in which an emulsion is prepared by emulsifying and dispersing the polyurethane and the (meth) acrylic monomer in an aqueous medium, and the (meth) acrylic monomer is subjected to emulsion polymerization in the resulting emulsion. At this time, the U/A resin is obtained as an aqueous dispersion of the U/A resin.

There are cases where the chain extension reaction of the polyurethane occurs concurrently with the polymerization of the (meth)acrylic monomer, due to water contained in the emulsion.

It is also possible to add the above mentioned chain extender in the emulsion to allow the chain extension reaction to proceed. The chain extension reaction may be carried out before or after the polymerization of the (meth) acrylic monomer.

As the radical polymerization initiator to be used in the polymerization reaction, the same radical polymerization initiator as used in the production of the U/A resin and the aqueous dispersion of the U/A resin according to the first invention can be used.

Further, the polymerization is carried out usually at a temperature of from 10 to 80° C., and preferably from 30 to 60° C. By maintaining the temperature at 40 to 90° C. for about 30 minutes to 3 hours after the generation of exothermic heat has completed, the polymerization will largely be completed. Thus, the aqueous emulsion of the U/A resin is obtained.

<Urethane Component of U/A Resin and Aqueous Dispersion of U/A Resin According to the Second Invention>

The urethane component of the U/A resin and the aqueous dispersion of the U/A resin according to the second invention contains a polyurethane containing a constituent component derived from the polyester polyol containing the phthalic acid-based unit, and the content percentage of the polyurethane in the urethane component contained in the U/A resin is preferably 50% by weight or more, more preferably 70% by weight or more, and still more preferably 85% by weight or more. It is most preferred that the urethane component be entirely composed of the polyurethane.

The urethane component excluding the above mentioned polyurethane containing a constituent component derived from the polyester polyol containing the phthalic acid-based unit is not particularly limited, as long as the object and the effect of the present invention is not impaired.

Further, in the present invention, the content of the structural unit derived from the dicarboxylic acid (dicarboxylic acid unit) contained in the polyurethane, among the constituent components of the U/A resin, is preferably 0.05% by weight or more and 50% by weight or less, more preferably 0.08% by weight or more and 40% by weight or less, and particularly preferably 0.1% by weight or more and 35% by weight or less, as described above. By adjusting the content of the dicarboxylic acid unit within the above mentioned range, the resulting U/A resin of the present invention can have an excellent flexibility, and particularly excellent strength and oil resistance.

It is also preferred that the content of the structural unit derived from the dicarboxylic acid (dicarboxylic acid unit) contained in the polyol component in the above mentioned polyurethane be within the same range, for the same reasons.

This is because, in the U/A resin, the component responsible for determining the oil resistance is a component derived from the polyurethane, and improving the oil resistance of the polyurethane leads to improving the oil resistance of the entire U/A resin.

Further, the dicarboxylic acid unit is a unit derived from at least one type selected from the group consisting of phthalic acid, isophthalic acid and terephthalic acid. In particular, the dicarboxylic acid unit is preferably an isophthalic acid unit, in terms of oil resistance.

The content of the dicarboxylic acid unit can be calculated according to the above mentioned method for calculating the content of the phthalic acid-based constituent component in the polyester polyol, from the composition of the U/A resin and the content of this unit in the urethane.

As the component (B) and other monomer(s) other than the component (B) used in this reaction, the same components as those described as the component (B) and other monomer(s) other than the component (B) to be used in the U/A resin and the aqueous dispersion of the U/A resin according to the above mentioned first invention, can be used.

The glass transition temperature (Tg) of the homopolymer or copolymer comprising the component (B) as a major component is preferably −50° C. or more, and more preferably −40° C. or more. If the Tg is lower than −50° C., the obtained cosmetic may have a sticky feel when touched, possibly resulting in a poor texture.

On the other hand, the glass transition temperature (Tg) thereof is preferably 120° C. or less, and more preferably 110° C. or less. A glass transition temperature exceeding 120° C. may result in a higher minimum film forming temperature, and there are cases where a uniform film may not be obtained. By controlling the glass transition temperature to be within the above mentioned range, even when used in a cosmetic having a high oil content, the plasticization of the polymer due to oil component can be prevented without greatly compromising the performance as a cosmetic. The glass transition temperature (Tg) can be measured or calculated using the measuring method or the calculation method of the glass transition temperature (Tg) described in the above mentioned U/A resin and the aqueous dispersion of the U/A resin according to the first invention.

In cases where a plurality of types of (meth)acrylic monomers are used, it is possible to adjust the flexibility of the film, by using a monomer whose homopolymer has a high Tg, and a monomer whose homopolymer has a low Tg in combination.

In this case, the Tg of the homopolymer of one of the monomers is preferably 95° C. or more and 150° C. or less, more preferably 100° C. or more and 140° C. or less; and the Tg of the homopolymer of the other monomer is preferably −70° C. or more and 30° C. or less, and more preferably −60° C. or more and 10° C. or less.

If the Tg of the monomer having a higher Tg is too high, the resulting film may be too hard, and if the Tg of the monomer having a lower Tg is too low, the film may be sticky.

<Characteristics of U/A Resin and Aqueous Dispersion of U/A Resin According to the Second Invention>

Next, the U/A resin and the aqueous dispersion of the U/A resin according to the present invention will be described.

The U/A resin of the present invention has an excellent oil resistance, since it includes a polyester polyol as the polyol component in the urethane component; and the polyester polyol contains a structural unit derived from at least one type of dicarboxylic acid selected from the group consisting of phthalic acid, isophthalic acid and terephthalic acid, in other words, the polyester polyol contains a constituent component derived from a phthalic acid-based polyester component, in particular an isophthalic acid-based polyester component.

The composition ratio of the polyurethane component to the (meth)acrylic component in the U/A resin in weight ratio, polyurethane component/(meth)acrylic component, is preferably from 80/20 to 30/70, and more preferably from 70/30 to 35/65. Note that, the total amount of the polyurethane component and the (meth)acrylic component is taken as 100.

If the amount of the polyurethane component, with respect to 100 of the total amount of the polyurethane component and the (meth)acrylic component, is greater than 80, the thermal reversibility (including the setting properties) when used as a hair styling agent may be deteriorated. On the other hand, if the amount of the polyurethane component, with respect to 100 of the total amount of the polyurethane component and the (meth)acrylic component, is less than 30, there are cases where the emulsification stability during the production of the U/A resin may be insufficient, or the aqueous emulsion to be produced may not be uniform.

In cases where the U/A resin is used as an aqueous emulsion, the concentration thereof is not particularly limited. However, it is preferred that the concentration be adjusted such that the content of a non-volatile component(s) in the emulsion is 20% by weight or more, more preferably 30% by weight or more. If the content of the non-volatile component is less than 20% by weight, there are cases where a longer time is required for drying. The upper limit thereof, on the other hand, is preferably 70% by weight or less, and more preferably 60% by weight or less. If the content of the non-volatile component exceeds 70% by weight, the resulting emulsion may be unstable.

Further, the minimum film forming temperature of the U/A resin is preferably 10° C. or less, and more preferably 5° C. or less. If the minimum film forming temperature is higher than 10° C., the resulting film may have an insufficient flexibility. At the same time, the minimum film forming temperature is preferably −20° C. or more, and more preferably −10° C. or more. If the minimum film forming temperature is less than −20° C., the thermal reversibility (including the setting properties) of the resulting film may be deteriorated.

A variety of methods can be used in order to adjust the minimum film forming temperature of the U/A resin within the above mentioned suitable range. As the methods for lowering the minimum film forming temperature, for example, the following (a) to (c) can be mentioned. It should be noted that the opposite approaches to the following methods can be taken in order to raise the minimum film forming temperature.

(a) As the polyol unit, a polyol(s) having a relatively high molecular weight, for example, one/those having a molecular weight of greater than 1,000 is/are used, or the amount thereof to be used is increased.

(b) The equivalent ratio of the polyol unit to the polyvalent isocyanate compound in the polyurethane is adjusted so as to be close to 1:1.

(c) As the (meth)acrylic monomer component, one/those having a low glass transition temperature (Tg) is/are used.

Further, the deodorization step of the U/A resin and the aqueous dispersion of the U/A resin is preferably carried out in the same manner as the deodorization step of the above mentioned U/A resin and the aqueous dispersion of the U/A resin according to the first invention.

The aqueous dispersion of the U/A resin in which the residual amount of the (meth)acrylic monomer component is thus reduced to 100 weight ppm or less, will be virtually odorless when used in a cosmetic, such as a hair styling agent, and accordingly, it can be suitably used as a raw material therefor.

As described above, film formation by casting of a mixed solution of the U/A resin and a silicone oil, such as cyclopentasiloxane, prepared at a weight ratio of 50/50, is possible at 23° C.

The weight average molecular weight (Mw) of the U/A resin is preferably 100,000 or more, and more preferably 150,000 or more. Further, the upper limit of the weight average molecular weight is preferably 2,000,000, more preferably 1,000,000, and still more preferably 800,000. If the weight average molecular weight is within the above mentioned range, it is possible to obtain an excellent mechanical stability, and an excellent pigment stability when a pigment is added thereto.

A weight average molecular weight of less than 100,000, on the other hand, may result in a poor pigment dispersibility. Further, a weight average molecular weight of greater than 2,000,000 tends to produce a hard and brittle film, possibly resulting in a poor texture. By adjusting the weight average molecular weight (Mw) within the above mentioned range, a particularly excellent oil resistance (film formability by casting) can be obtained.

In addition, the molecular weight distribution (Mw/Mn) of the U/A resin is usually 1.5 or more and 2.5 or less, and preferably 1.7 or more and 2 or less.

By adjusting the molecular weight distribution within this range, it is possible to reduce the stickiness due to the low molecular weight component and the stiffness due to the high molecular weight component in the resulting product, thereby improving the feeling upon use particularly when used in a cosmetic for skin.

Further, the most frequently observed molecular weight, of the weight average molecular weights (Mw) of the urethane component contained in the U/A composite resin, in other words, in a chart (chromatogram) obtained by measuring the Mw of the U/A composite resin by gel permeation chromatography method (GPC method), as shown in FIG. 1, the molecular weight at the position of the peak (the portion of the graph shown in FIG. 1 as (A)) which corresponds to the polymer of the urethane component (hereinafter, the most frequently observed molecular weight of the polymer of the urethane component is referred to as the peak molecular weight (Mwp) of the polymer of the urethane component, and sometimes referred to as the "Mwp of the urethane component") is preferably 30,000 or more, and more preferably, 40,000 or more. If the Mwp of the urethane component is lower than 30,000, the long term stability of the U/A resin may be insufficient, and in an environment where the temperature rises above 30° C., for example, there is a potential risk that the degradation of the U/A resin may be accelerated. The upper limit of the Mw of the urethane component, on the other hand, is preferably 200,000, and more preferably 150,000. If the Mwp of the urethane component is greater than 200,000, there are cases where the U/A resin may be too hard, resulting in a poor texture, or the viscosity of the system may be increased excessively during the synthesizing step, resulting in a poor productivity.

In addition, the peak molecular weight (Mwp) of the polymer of the acrylic component (the portion of the graph shown in FIG. 1 as (B), hereinafter, sometimes referred to as the "Mwp of the acrylic component) contained in this U/A composite resin is preferably 200,000 or more, and more preferably 300,000 or more. If the Mwp of the acrylic component is lower than 200,000, the 1,3BG resistance and/or the pigment dispersibility of the U/A resin may be deteriorated. The upper limit of the Mwp of the acrylic component, on the other hand, is preferably 2,000,000, and more preferably 1,000,000. If the Mwp of the acrylic component is higher than 2,000,000, the resulting film tends to be hard and brittle, possibly resulting in a poor texture.

Further, it is preferred that there is an appropriate difference between the peak molecular weight (Mwp) of the acrylic component and the peak molecular weight (Mwp) of the urethane component contained in this U/A composite resin, and the difference therebetween ((Mwp of acrylic component)–(Mwp of urethane component)) is preferably 200,000 or more, and more preferably 250,000 or more. If the above mentioned difference is less than 200,000, the mechanical stability of the U/A resin may be insufficient. The upper limit of the difference, on the other hand, is preferably 2,000,000, and more preferably 1,000,000. If the difference is greater than 2,000,000, the resulting film tends to be hard and brittle, possibly resulting in a poor texture, due to the influence of the polymer having a higher molecular weight.

Note that, the "1,3BG resistance" has the same meaning as described above.

When the (meth)acrylate-based polymerizable monomer, which is the component (B), is subjected to emulsion polymerization in an aqueous medium, a chain transfer reaction to the polymerization initiator, emulsifying agent and/or the like, and/or to the other polymers generated, in the aqueous medium, is likely to occur during the polymerization, and there are cases where the molecular weight of the resulting polymer is reduced.

However, since in the present invention, a pre-emulsion is prepared by emulsifying and dispersing the component (A) (polyurethane containing an isocyanate group and a carboxyl group) and the component (B) ((meth)acrylate-based polymerizable monomer) in an aqueous medium, and the component (B) is polymerized in the pre-emulsion to produce the aqueous dispersion of the urethane-(meth)acrylic composite resin (U/A resin aqueous dispersion), the radical polymerization occurs in the situation where the component (B) being present inside the component (A) within emulsion droplets. At this time, since the component (B) is protected by the component (A), the chain transfer reaction is less likely to occur in the component (B) during the polymerization. In addition, since the polymerization is allowed to proceed under the conditions where a polymerization termination reaction is less likely to occur, the molecular weight of the component (B) tends to be increased. Thus, a composite resin having a core-shell structure in which the urethane resin forms a shell portion, and the (meth)acrylic resin forms a core portion, is obtained. The molecular weight of the component (B) at this time tends to be higher as compared to the molecular weight thereof when subjected to emulsion polymerization in the absence of the component (A), and the molecular weight distribution of the resulting composite resin will exhibit two peaks, as shown in FIG. 1. Not that, the horizontal axis (RT mm) in the graph shown in FIG. 1 represents the retention time (min), and it is shown that the shorter the RT, the higher the molecular weight.

The molecular weight distribution of the above mentioned composite resin is as shown in FIG. 1, and the position of each of the peaks, in other words, the relationship between the Mwp of the acrylic component and the Mwp of the urethane component is as described above.

In cases where it is difficult to clearly discriminate the peak molecular weight (Mwp) of the urethane component from the peak molecular weight (Mwp) of the acrylic component contained in the U/A composite resin, in other words, when two peaks are not clearly observed in the chart (chromatogram) of the U/A composite resin obtained by gel permeation chromatography method (GPC method), as shown in FIG. 1, the urethane component and the acrylic component may be separately subjected to polymerization under the corresponding conditions to obtain respective aqueous dispersions, followed by measuring the Mw of the respective components by gel permeation chromatography method (GPC method) to obtain chromatograms, and the molecular weight at the position of the peak in each of the chromatograms may be defined as the peak molecular weight (Mwp) of the urethane component or the peak molecular weight (Mwp) of the acrylic component. It should be noted, however, the measured value of the Mwp of the acrylic component (component (B)), in particular, will usually be lower than the actual value, in this case, because the above described effect of increasing the molecular weight is not provided.

The above mentioned U/A resin preferably contains a component (gel fraction) which does not dissolve in THF (tetrahydrofuran). The gel fraction is preferably 10% by weight or more, and more preferably 30% by weight or more. Too low a gel fraction could possibly result in a poor blending stability and/or oil resistance.

The upper limit of the gel fraction is not particularly limited, and it may be 100% by weight, but preferably 99% by weight or less. By adjusting the gel fraction within the above mentioned range, the above described oil resistance (film formability by casting) is further improved. This property can be obtained particularly effectively, by controlling the weight average molecular weight (Mw) of the U/A resin to be within the above mentioned range.

<Main Applications of U/A Resin or Aqueous Dispersion of U/A Resin>

The U/A resin or the aqueous dispersion of the U/A resin according to the present invention can be suitably used in the following applications. In particular, the U/A resin or the aqueous dispersion of the U/A resin according to the second invention exhibits an excellent oil resistance as described above, due to containing a phthalic acid unit, particularly, an isophthalic acid unit, as well as an excellent mechanical stability (stability of the emulsion) and the pigment dispersibility, possibly due to comprising the polyurethane having a self-emulsifying ability.

(1) Cosmetics

The U/A resin or the aqueous dispersion of the U/A resin according to the first invention and the second invention of the present invention can be suitably used as a resin for use in a cosmetic, such as a hair cosmetic or a skin cosmetic. The usage thereof will now be described in brief.

[Hair Cosmetics]

When used as a resin for use in a hair cosmetic, the U/A resin or the aqueous dispersion of the U/A resin according to the present invention is added to a hair cosmetic, such as a well-known shampoo, a hair rinse, a treatment product, a hair setting agent, and a permanent wave solution, to be used. At this time, a conventionally used, well-known polymer(s) may be used in combination. The hair cosmetic to which the U/A resin or the aqueous dispersion of the U/A resin is added may be in any form, such as a liquid, cream, emulsion, spray, gel, mousse (cream/gel-like product capable of being ejected in the form of foam) and the like.

The amount of the U/A resin or the aqueous dispersion of the U/A resin to be added varies depending on the form and the purpose of the hair cosmetic, or the type and the amount of the polymer to be used in combination. However, it is preferably added such that the amount of the resin contained in the aqueous dispersion of the U/A resin for use in a cosmetic, with respect to the amount of the hair cosmetic, is from 0.05 to 10% by weight, and more preferably 0.1 to 8% by weight.

Further, the U/A resin or the aqueous dispersion of the U/A resin can be used alone, or in combination with a conventionally used, well-known hair setting polymer(s) of anionic, nonionic, cationic or amphoteric ionicity. The hair setting polymer to be used in combination is more preferably an anionic or nonionic hair setting polymer, in terms of mixing stability.

Examples of the anionic polymer to be used as the hair setting polymer include: a copolymer of a (meth)acrylic acid and an alkyl methacrylate (trade name: DIAHOLD (manufactured by Mitsubishi Chemical Corporation), trade name: Plascize L-53 series, etc. (manufactured by GOO Chemical CO., Ltd.); a copolymer of maleic acid monoalkyl ester and methyl vinyl ether (trade name: GANTREZ AN-119 (manufactured by ISP Japan Ltd.); and the like.

Examples of the nonionic polymer to be used as the hair setting polymer include: polyvinyl pyrrolidone polymer (trade name: PVP series (manufactured by ISP Japan Ltd.); a copolymer of vinyl pyrrolidone and vinyl acetate (trade name: LUVISKOL VA series (manufactured by BASF Japan Ltd.); and the like. Examples of the amphoteric polymer to be used as the hair setting polymer include: a methacrylate copolymer (trade name: YUKAFORMER series (manufactured by Mitsubishi Chemical Corporation)), and the like.

Examples of the cationic polymer to be used as the hair setting polymer include: an ether of hydroxy cellulose and glycidyl trimethylammonium chloride (trade name: Leoguard G (manufactured by Lion Corporation), trade name: Polymer JR-30M-125 and JR-30M-400 (manufactured by Union Carbide Corporation)); a quaternized product of vinyl pyrrolidone-dimethylaminoethyl methacrylate copolymer (trade name: GAFQUAT 734 and 755 (manufactured by ISP Japan Ltd.); a dimethyl diallyl ammonium chloride polymer (trade name: MERQUAT 100 (manufactured by Lubrizol Corporation)), a dimethyl diallyl ammonium chloride acrylamide copolymer (trade name: MERQUAT550 (manufactured by Lubrizol Corporation)); and the like.

Examples of the hair setting cosmetic in which the U/A resin or the aqueous dispersion of the U/A resin and the hair setting polymer are used in combination include various types of hair styling agents containing water and/or alcohols such as ethanol, isopropanol and the like, for example: aerosol hair sprays, pump type hair sprays, foam type hair sprays, hair mists, hair setting lotions, hair creams, and hair oils.

In cases where the hair styling agent is prepared in the form of a hair cosmetic capable of being ejected in the form of foam (mousse), the following composition is used, for example: from 0.01 to 10% by weight (solids content) of the U/A resin or the aqueous dispersion of the U/A resin; from 0 to 15% by weight of a known hair setting polymer; from 0.1 to 5% by weight of a nonionic surface active agent; from 3 to 25% by weight of a liquefied gas; and from 60% by weight to the balance of a water soluble solvent composed mainly of water (it should be noted, however, water content in the hair cosmetic is 60% by weight or more).

Examples of the nonionic surface active agent to be used include: sorbitan fatty acid ester, glycerin fatty acid ester, polyoxyethylene sorbitan fatty acid ester, polyethylene glycol fatty acid ester, polyoxyethylene alkyl ether, polyoxyethylene alkyl phenyl ether, polyoxyethylene castor oil, polyoxyethylene hydrogenated castor oil, fatty acid alkanol amide, and the like.

In cases where the hair styling agent is prepared in the form of a gel, the following composition is used, for example: from 0.01 to 10% by weight (solids content) of the U/A resin or the aqueous dispersion of the U/A resin; from 0 to 15% by weight of a hair setting polymer; from 0.1 to 3% by weight of a gel base; and from 72% by weight to the balance of water.

In cases where the hair styling agent is prepared as a hair spray, the following composition is used, for example: from 0.01 to 10% by weight (solids content) of the U/A resin or the aqueous dispersion of the U/A resin; from 0 to 15% by weight of a hair setting polymer; from 30 to 80% by weight of an organic solvent, and from 10 to 70% by weight of a propellant.

Examples of the propellant which can be used in the above mentioned hair spray and mousse include: ethanol; liquefied gases such as liquefied petroleum gas, dimethyl ether, and halogenated hydrocarbons; compressed gases such as air, carbon dioxide, and nitrogen gas; and the like.

The U/A resin or the aqueous dispersion of the U/A resin of the present invention can be used in a conditioning cosmetic, such as a shampoo, a conditioner (hair rinse), a permanent wave solution and the like. Such a hair cosmetic often contains, for example, water and/or an alcohol such as ethanol or isopropanol as a solvent, and in addition, a hydrocarbon having a boiling point of from 50° C. to 300° C. In these conditioning cosmetics, as with the above described hair setting cosmetics, the U/A resin or the aqueous dispersion of the U/A resin is used alone, or in combination with a conventionally used conditioning polymer(s) of anionic, nonionic, cationic or amphoteric ionicity. As the hair setting polymer to be used in combination, an anionic or nonionic hair setting polymer is more preferred in terms of mixing stability.

When used in a shampoo, the U/A resin or the aqueous dispersion of the U/A resin can be added to an anionic, amphoteric or nonionic surface active agent to be used in the shampoo. Examples of the anionic surface active agent used in a shampoo include: N-fatty acid acyl-N-methyl-β-alanine salts such as N-coconoil-N-methyl-β-alanine sodium, N-myristoyl-N-methyl-β-alanine sodium, and the like.

Examples of the amphoteric surface active agent include: coco acid propyl betaine, dimethyl lauryl betaine, bis(2-hydroxyethyl)lauryl betaine, cyclohexyl laurylamine oxide, dimethyl laurylamine oxide, bis(2-hydroxyethyl)laurylamine oxide, and the like.

Examples of the nonionic surface active agent include: stearic acid diethanol amide, coconut fatty acid diethanol amide, sorbitan sesquioleate, polyoxyethylene stearyl ether, and the like.

When used in a hair rinse, the U/A resin or the aqueous dispersion of the U/A resin according to the present invention can be added to a cationic surface active agent to be used in the hair rinse. Examples of the cationic surface active agent include: stearyltrimethylammonium chloride, di stearyldimethylammonium chloride, stearyldimethylbenzylammonium chloride, and the like.

Further, when used in a permanent wave solution, the U/A resin or the aqueous dispersion of the U/A resin is added to an oxidizing agent such as a bromate and a perborate; and a reducing agent such as thioglycolic acid and the salt thereof, and cysteine.

In addition to the above, when used as a hair treatment, for example, the U/A resin or the aqueous dispersion of the U/A resin of the present invention can be used in combination with, or instead of, a cationic surface active agent, and/or a cationized polymer such as a cationic polypeptide, cationic cellulose, or cationic polysiloxane. As the above mentioned cationic surface active agent, for example, those mentioned above for use in a hair rinse can be used without any particular problem.

Both of the above mentioned hair setting cosmetic and the conditioning cosmetic may contain another arbitrary component(s), in addition to the above mentioned various types of components as necessary, to the extent that the effect of the present invention is not impaired. Examples of the arbitrary component include: hydrocarbons, linear alcohols, branched alcohols, higher fatty acids and derivatives thereof, plant-based polymers, microorganism-based polymers, naturally-occurring water soluble polymers, cellulose-based polymers, semisynthetic water soluble polymers, vinyl-based polymers, polyoxyethylene-based polymers, synthetic water soluble polymers, inorganic water soluble polymers, silicones, N-fatty acid acyl-L-glutamates, N-fatty acid-N-methyltaurine salts, salts of N-fatty acid sarcosine condensate, surface active agents other than the above mentioned surface active agents, emulsifying agents, humectants, antibacterial agents, vasodilators, agents for imparting refreshing feeling, agents for imparting feeling of stimulation, vitamins, sterilizing antiseptics, chelating agents, pH adjusting agents, foam increasing agents, foaming agents, foam stabilizers, and the like. Further, in cases where these cosmetics are prepared in the form of an aerosol, a propellant such as liquefied petroleum gas or dimethyl ether is used in combination. In addition, a metal ion scavenger, a fungicide, a bactericide, an opacifier, a conditioning agent, a thickener, an antioxidant, a solubilizer, a rosin, a hydrotrope, a hair growth stimulant, a herbal medicine, a pigment, and/or a perfume may be used, depending on the application and the purpose.

Examples of the hydrocarbons include: liquid paraffin, vaseline, solid paraffin, squalane, olefin oligomer, and the like. Examples of the linear alcohol include: lauryl alcohol, cetyl alcohol, stearyl alcohol, behenyl alcohol, myristyl alcohol, oleyl alcohol, cetostearyl alcohol, and the like.

Examples of the branched alcohol include: monostearyl glycerin ether, 2-decyltetradecynol, lanolin alcohol, cholesterol, phytosterol, hexyl dodecanol, isostearyl alcohol, octyl dodecanol, and the like.

Examples of the higher fatty acids and derivatives thereof include: lauric acid, myristic acid, palmitic acid, stearic acid, behenic acid (behenyl acid), oleic acid, 1,2-hydroxystearic acid, undecylenic acid, tall acid, lanolin fatty acid, isostearic acid, linoleic acid, linoleynoic acid, γ-linolenic acid, eicosapentaenoic acid, and the like.

Examples of the plant-based polymer include: carrageenan, pectin, agar, quince seed (quince), algae colloid (brown algae extract), starch (rice, corn, potato, wheat), glycyrrhizic acid, and the like.

Examples of the microorganism-based polymer include: xanthan gum, dextran, pullulan, and the like. Examples of the naturally-occurring water soluble polymer include: animal-based polymers such as collagen and gelatin; and the like. Examples of the cellulose-based polymer include: methyl cellulose, ethyl cellulose, methylhydroxypropyl cellulose, hydroxyethyl cellulose, sodium cellulose sulfate, hydroxypropyl cellulose, sodium carboxymethyl cellulose (CMC), crystalline cellulose, cellulose powder, and the like.

Examples of the semisynthetic water soluble polymer include: alginic acid-based polymers such as sodium alginate and propylene glycol alginate; and the like. Examples of the vinyl-based polymer include: polyvinyl alcohol, polyvinyl methyl ether, polyvinyl pyrrolidone, carboxyvinyl polymer (Carbopol), and the like.

Examples of the polyoxyethylene-based polymer include: polyethylene glycol 20,000, 40,000, 60,000 and the like. Examples of the synthetic water soluble polymer include: polyethyleneimine and the like. Examples of the inorganic water soluble polymer include: bentonite, magnesium aluminum silicate (bee gum), rabonite, hectorite, silicic anhydride and the like.

Examples of the silicones include: volatile silicone oils, silicone resins, silicone gums, alkyl-modified silicones and the like. Examples of the N-fatty acid acyl-L-glutamate include: monosodium N-lauryl-L-glutamate, N-coconut oil fatty acid-L-glutamic acid monotriethanolamine, monosodium N-myristyric acid acyl-L-glutamate, monosodium N-mixed fatty acid acyl-L-glutamate, and the like.

Examples of the N-fatty acid-N-methyltaurine salt include: lauric acid methyl taurine sodium, coconut oil fatty acid methyl taurine sodium, and the like. Examples of the salt of N-fatty acid sarcosine condensate include: sodium lauroyl sarcosine, sodium cocoyl sarcosine, and the like.

Examples of the other surface active agents include: acyl sarcosine sodium, acyl glutamate, sodium acyl-β-alanine, acyl taurate, lauryl sulfate, lauryldimethylaminoacetic betaine, alkyltrimethyl ammonium chloride, and polyoxyethylene hydrogenated castor oil, and the like.

Examples of the emulsifying agent include: glyceryl monostearate, sorbitan monopalmitate, polyoxyethylene cetyl ether, polyoxyethylene sorbitan monolaurate, and the like.

Examples of the humectant include (poly)ethylene glycol, (poly)propylene glycol, glycerin, 1,3-butylene glycol, maltitol, sorbitol, chondroitin sulfuric acid, hyaluronic acid, atelocollagen, cholesteryl-1,2-hydroxystearate, sodium lactate, bile salt, dl-pyrrolidone carboxylate, short-chain soluble collagen, and the like.

Examples of the antibacterial agent include: hinokitiol, hexachlorophene, benzalkonium chloride, trichlorocarbanilide, bithionol and the like. Examples of the vasodilator include carpronium chloride and the like. Examples of the agent for imparting refreshing feeling include: menthols and the like. Examples of the agent for imparting feeling of stimulation include: benzyl nicotinate and the like. Examples of the vitamins include vitamin A, B, C, D, E and the like.

Examples of the sterilizing antiseptic include: chlorhexidine gluconate, isopropyl methyl phenol, paraoxybenzoate, and the like. Examples of the chelating agent include: protein hydrolysates, amino acids, plant extracts, EDTA-Na, and the like. Examples of the pH adjusting agent include: succinic acid, sodium succinate, triethanolamine, and the like.

Next, skin cosmetics and make-up cosmetics will be described, which are other applications of the U/A resin or the aqueous dispersion of the U/A resin according to the present invention.

[Skin Cosmetics]

When used as a resin for use in a skin cosmetic, the U/A resin or the aqueous dispersion of the U/A resin according to the present invention is added to a skin cosmetic product, such as a skin cream, a lotion or an emulsion.

[Make-Up Cosmetics]

Examples of the make-up cosmetics include: mascaras, eye liners, eye shadows, lipsticks, lip glosses, make-up foundations, make-up rouges and the like. These make-up cosmetics can be obtained by adding materials usually used in cosmetics to the U/A resin or the aqueous dispersion of the U/A resin of the present invention, depending on the applications and the purposes, followed by mixing. Examples of the materials include: oil components such as solid oils, fats and oils, waxes, and silicone oils;

powder components such as pigments; and solvents such as liquid alcohols.

In cases where the U/A resin or the aqueous dispersion of the U/A resin according to the first invention is used, examples of the above mentioned powder components such as pigments include the following:

(1) Pigments such as Red No. 104, Red No. 102, Red No. 226, Red No. 201, Red No. 202, Yellow No. 4, and Black No. 401;

(2) Lake pigments such as Blue No. 1 aluminum lake, Yellow No. 4 aluminum lake, Yellow No. 5 aluminum lake, and Yellow No. 203 barium lake;

(3) Polymers in the form of powder such as nylon powder, silk powder, urethane powder, Teflon (registered trademark) powder, silicone powder, methyl polymethacrylate powder, cellulose powder, silicone elastomer spherical powder, and polyethylene spherical powder;

(4) Colored pigments such as yellow iron oxide, red iron oxide, black iron oxide, chromium oxide, carbon black, ultramarine, and Prussian blue;

(5) White pigments such as zinc oxide, titanium oxide, and cerium oxide; and extender pigments such as talc, mica, sericite, kaolin, and plate-like barium sulfate;

(6) Pearl pigments such as titanated mica, red iron oxide-coated titanated mica, carmine-coated titanated mica, Prussian blue-coated titanated mica, and black iron oxide-coated titanated mica;

(7) Metal salts such as barium sulfate, calcium carbonate, magnesium carbonate, aluminum silicate, and magnesium silicate;

(8) Inorganic powders such as silica and alumina; and (9) Bentonite, smectite, boron nitride, lauroyl lysine, fine particles of titanium oxide, fine particles of zinc oxide, and the like.

The particle size of these powders is preferably within the range of from 5 nm to 100 μm, and more preferably, within the range of from 10 nm to 50 μm. The shape of the powders (such as in the form of spheres, sticks, needles, plates, amorphous, scales, or spindles) is not particularly limited.

Each of the above mentioned various types of powders may be mixed to the U/A resin individually, or alternatively, a mixture of the powder components may be prepared in advance, followed by blending to the resin.

Further, a mixture whose color has been adjusted to a desired color, such as skin color, may be used. In addition, ultraviolet light scattering components such as fine particles of titanium oxide and fine particles of zinc oxide may be added to impart an ultraviolet prevention function to the resulting blend.

Examples of the above mentioned oil components such as solid oils include volatile or non-volatile oils, solvents, and resins, usually used in cosmetics, and these may be in any form, for example, a liquid, a paste, or a solid at normal temperature.

Examples of the oil components which can be used in the present invention include the following:

(1) Fatty acids such as isostearic acid, undecylenic acid, and oleic acid;

(2) Fatty acid esters such as myristyl myristate, hexyl laurate, decyl oleate, isopropyl myristate, hexyldecyl dimethyloctanoate, glycerin monostearate, diethyl phthalate, monostearate ethylene glycol, and octyl oxystearate;

(3) Higher hydrocarbons such as liquid paraffin, paraffin, vaseline, and squalane; so-called waxes such as lanolin, reduced lanolin, carnauba wax, candelilla wax, Ceresin, Ozocerite, and microcrystalline wax; and fats and oils such as mink oil, cacao butter, coconut oil, palm kernel oil, camellia oil, sesame oil, castor oil, and olive oil;

(4) Synthetic polymers having a middle to low molecular weight, such as polyethylene waxes, ethylene.α-olefin co-oligomers, and ethylene propylene copolymers;

(5) Silicone oils and silicone compounds such as cyclic silicones, dimethylpolysiloxane, methyl hydrogen polysiloxane, methyl phenyl polysiloxane, polyether-modified organopolysiloxane, alkyl-modified organopolysiloxane, terminal-modified organopolysiloxane, polyglyceryl-modified silicone, amodimethicone, amino-modified organopolysiloxane, silicone gel, acrylic silicone, and trimethylsiloxysilicic acid; and (6) Fluorine compounds such as perfluoropolyethers, fluorocarbons, and fluoroalcohols.

Examples of the above mentioned solvents such as liquid alcohols include the following:

(1) Lower alcohols: ethanol, isopropyl alcohol and the like;

(2) Higher alcohols: cetyl alcohol, isostearyl alcohol, lauryl alcohol, hexadecyl alcohol, octyl dodecanol, and the like;

(3) Polyols: glycerin, sorbitol, ethylene glycol, propylene glycol, 1.3 butylene glycol, polyethylene glycol, and the like; and (4) Other solvents: water, light liquid isoparaffin, ethers, LPG, fluorocarbons, N-methylpyrrolidone, fluoroalcohols, volatile linear silicones, various types of chlorofluorocarbons and the like.

In addition to the above mentioned components, the cosmetic according to the present invention may contain, as appropriate, other components usually used in cosmetics, such as a fluorine compound, any of various types of resins, a surface active agent, a viscosity-imparting agent, an antiseptic, a perfume, an ultraviolet absorber (may be organic or inorganic-based; and may be corresponding to UV-A or UV-B), a bioactive component, a salt, an antioxidant, a chelating agent, a neutralizer, and/or a pH adjusting agent, to the extent that the object and the effect of the present invention are not impaired.

In cases where the U/A resin or the aqueous dispersion of the U/A resin according to the first invention is used, it is possible to provide various types of hair cosmetics, such as hair sprays, mousses, hair setting lotions, gels, and sprays, which are capable of providing an excellent hair setting effect and texture.

On the other hand, the U/A resin or the aqueous dispersion of the U/A resin according to the second invention can be suitably used for skin cosmetics, such as liquid foundations, skin creams, UV care creams, and skin lotions, since the U/A resin is capable of forming a flexible film.

Further, since the U/A resin exhibits an excellent film-forming ability even when used in cosmetics containing a large amount of an oily component, due to its excellent oil resistance, it is suitable for use in mascaras, eye liners, and the like.

The U/A resin of the present invention can also be used in cosmetics other than those mentioned above. In that case, the cosmetic may contain components for use in a cosmetic, such as a fluorine compound, any of various types of resins, a surface active agent, a viscosity-imparting agent, an antiseptic, a perfume, an organic/inorganic-based ultraviolet absorber, a bioactive component, a salt, an antioxidant, a chelating agent, a neutralizer, and/or a pH adjusting agent, to the extent that the object and the effect of the present invention are not impaired.

[Other Applications]

The U/A resin or the aqueous dispersion of the U/A resin according to the second invention can be used in coatings such as industrial coatings (coatings for automobiles, in particular) and coatings for household use, coating agents, protective film forming agents, and the like, taking advantage of its properties such as oil resistance, flexibility, adherence, conformability to base materials, wear resistance and the like.

EXAMPLES

The present invention will now be specifically described by way of Examples. However, the invention is not limited by the following Examples. First, raw materials to be used will be described.
<Polyurethane and U/A Resin or Aqueous Dispersion of U/A Resin According to the First Invention>

First, Examples of the polyurethane and the U/A resin or the aqueous dispersion of the U/A resin according to the first invention will be described.
<Polyol Units>

D1000 Trade name: HIFLEX D1000, polypropylene glycol (C3 polyol), number average molecular weight (Mn)=1,000, OHV=111; manufactured by DKS Co. Ltd.

D2000 Trade name: HIFLEX D2000, polypropylene glycol (C3 polyol) number average molecular weight (Mn)=2,000, OHV=55.8; manufactured by DKS Co. Ltd.

PEG1000 Trade name: PEG1000, polyethylene glycol (C2 polyol), number average molecular weight (Mn)=1,000, OHV=111; manufactured by NOF CORPORATION PTMG650 Polytetramethylene glycol (C4 polyol), number average molecular weight (Mn)=650, OHV=175; manufactured by Mitsubishi Chemical Corporation PTMG1000 Polytetramethylene glycol (C4 polyol), number average molecular weight (Mn)=1,000, OHV=111; manufactured by Mitsubishi Chemical Corporation;

PTMG2000 Polytetramethylene glycol (C4 polyol), number average molecular weight (Mn)=2,000, OHV=55.8; manufactured by Mitsubishi Chemical Corporation N4073 Trade name: NIPPOLLAN 4073, a polyester polyol of 1,6-hexandiol and adipic acid, number average molecular weight (Mn)=2,000, OHV=58.4; manufactured by Nippon Polyurethane Industry Co., Ltd.

Note that, in the above description, "OHV" refers to the hydroxyl value (OH Value), and the unit is in "mg KOH/g".
<Polyvalent Isocyanate Compound>

IPDI Trade name: VESTANAT IPDI (isophorone diisocyanate); manufactured by Degussa Japan Co., Ltd.
<Carboxyl Group-Containing Polyvalent Hydroxy Compound>

Bis-MPA Dimethylolpropionic acid (carboxylic acid-containing diol); manufactured by Perstorp Japan Co., Ltd.
<Polymerization Inhibitor>

MEHQ 2-methoxyhydroquinone; manufactured by Wako Pure Chemical Industries, Ltd.
<Polymerizable Monomers>

MMA Methyl methacrylate; manufactured by Mitsubishi Rayon Co., Ltd.

BA n-Butyl acrylate; manufactured by Mitsubishi Chemical Corporation
<Radical Polymerization Initiator> tBPO Di-tert-butyl peroxide; manufactured by Kayaku Akzo Corporation
<Reducing Agent>

AsA L-ascorbic acid (special grade reagent); manufactured by Wako Pure Chemical Industries, Ltd.
<Basic Compounds>

KOH: potassium hydroxide (Reagent) manufactured by Wako Pure Chemical Industries, Ltd.

TEA: triethanolamine TEA99; manufactured by Shell Chemicals Japan Ltd.;
(Test Methods)

Each of the test methods will be described below.
<Number Average Molecular Weight of Polyol>

The number average molecular weight of each of the polyols was calculated from the hydroxyl value (OHV; unit: mg KOH/g) thereof, according to the following equation.

$$\text{Polyol } Mn = \text{formula weight of potassium hydroxide } (56.1)/\text{OHV of raw material} \times 2 \times 1{,}000$$

Note that, the hydroxyl value (OHV) was measured according to JIS K1557-1.
<Weight Average Molecular Weight and Molecular Weight Distribution of Component (A)>

The measurement of the weight average molecular weight (Mw) and the molecular weight distribution (Mw/Mn) was carried out, using the gel permeation chromatography method (GPC method), under the following conditions.

Measuring apparatus: LC-20AD (manufactured by Shimadzu Corporation)

Detector: RI (refractive index)

Column: PLgel Mixed B (manufactured by Agilent Technologies Inc.)

Developing solvent: THF (tetrahydrofuran)

Flow rate of developing solvent: 1 ml/min

Injected amount of measurement sample: 100 μL

Measurement sample: The resulting dispersion liquid of the urethane-(meth)acrylic composite resin is dried under the following drying conditions to prepare a dry sample, and then a 0.2% by weight solution of the dry sample is prepared using THF. The obtained solution is filtered using the filter described below, and the resulting filtrate is used as the measurement sample.

Drying conditions: Drying at 40° C. for 12 hours, followed by vacuum drying at room temperature for 6 hours Filter for preparation of measurement sample: GL chromatodisc (pore size: 0.45 μm) (manufactured by GL Sciences Inc.)

Calibration curve: In terms of PMMA (polymethyl methacrylate)

<Weight Average Molecular Weight (Mw), Molecular Weight Distribution (Mw/Mn) and Peak Molecular Weight (Mwp) of U/A Resin>

The measurement of the weight average molecular weight (Mw) and the molecular weight distribution (Mw/Mn) of the U/A resin were carried out in the same manner as described in the above mentioned <Weight average molecular weight of component (A)>.

Further, from the above mentioned GPC chart, the peak molecular weight (Mwp) of the component (A) and the peak molecular weight (Mwp) of the component (B) were measured.

<Measurement Method and Calculation Method of Acid Value>

The measurement of the acid value was carried out according to the potentiometric titration method (JIS-K-0070) using potassium hydroxide. In the measurement, "the amount of polyurethane" was used as the mass of the sample.

Further, since salt exchange is less likely to occur when potassium hydroxide is used in the neutralization step in the production of the polyurethane, for example, there are cases where it may be difficult to carry out the measurement according to the above mentioned method specified in JIS. In such a case, the "theoretical acid value" corresponding to 1 g of polyurethane was calculated according to the following equation, to be used as the acid value.

Theoretical acid value (mg KOH/g–polyurethane)
=number of moles of acid-containing raw material charged×56.1 (formula weight of KOH)/ amount of polyurethane (g)×1,000

<Gel Fraction>

A quantity of 40 mg of the dry sample obtained as described above is dissolved in 20 mL of THF, and the resultant is filtered using a gel filtration filter (manufactured by Advantec Co., Ltd.; PF-100: pore size: 100 μm).

The gel filtration filter after the filtration is dried at 105° C. for 3 hours, and an unused filter is also dried in the same manner, and the residual solids content is obtained based on the weights of these filters, and the gel fraction is calculated based on the following equation.

Gel fraction (% by weight)=(weight of filter after drying (mg)–weight of filter before use (mg))/ 40 (mg)×100

<Measurement Method and Calculation Method of MFT>

Referring to JIS K6828-2, the lowest temperature at which a uniform film without ruptures was formed after drying the aqueous dispersion was measured as the minimum film forming temperature (MFT).

Specifically, using a thermal gradient tester manufactured by Nichiri Co., Ltd., the resulting aqueous dispersion was coated with an applicator to a thickness of from 0.2 to 0.3 mm, and the moisture was allowed to dry. Then, the temperature corresponding to the border line above which a continuous film was formed and below which a non-continuous film was formed, was measured, to be defined as the MFT.

<Degree of Neutralization>

The degree of neutralization of the resulting polyurethane or the urethane-acrylic resin was calculated, from the number of moles of carboxyl groups contained, based on the charged amount of the component (A), and from the number of equivalent of the neutralizer (such as KOH) used in the neutralization of the carboxyl groups, as previously described in the first neutralization step and the second neutralization step herein.

It is also possible to obtain the degree of neutralization experimentally, from the content of the acid component measured by neutralization titration, which is commonly used, and the charged amount of the component (A).

<Glass Transition Temperature (Tg)>

[Component (A)]

The measurement was carried out according to JIS K 7244-4.

[Component (B)]

The Tg of the polymer was calculated from the Tg and the weight fraction of the homopolymer of each of the polymerizable monomers used, according to the following equation (1) (FOX equation):

$$1/Tg=(Wa/Tga)+(Wb/Tgb)+(Wc/Tgc)+\ldots \quad (1)$$

wherein Tg represents the glass transition temperature (K) of (co)polymer; each of Tga, Tgb, Tgc and the like represents the glass transition temperature (K) of the homopolymer of each of the constituent monomers a, b, c and the like; and each of Wa, Wb, Wc and the like represents the weight fraction of each of the constituent monomers a, b, and c in the copolymer.

As described above, in cases where the Tg needs to be expressed in "° C.", it can be calculated by subtracting "273" from the numerical value of the Tg obtained by the above equation.

<Physical Properties of Film>

[Drying Properties]

The resulting aqueous dispersion was diluted with pure water to a solids concentration of 30% by weight, to obtain a sample liquid. Then, in a constant temperature and humidity chamber controlled to 23° C. and 50% RH, the obtained sample liquid was coated on a polyester film (PET film) using a 0.05 mm applicator such that the coated area would be 40 cm². One minute after the coating, the weight thereof was measured and the dryness fraction (%) was calculated.

Dryness fraction (%)=(weight after one minute–theoretical solids content)×100/(initial weight–theoretical solids content)

[Stress-Strain (S-S)]

(1) Preparation of Test Specimen

The sample (aqueous dispersion) is coated on a plate made of polypropylene and the resultant is left to stand overnight at room temperature, such that the thickness of the resulting dried film would be 200 The resulting film is peeled off, and dried for 6 hours using a vacuum dryer.

(2) Test Method

The dried film obtained as described above was cut in the form of a strip having a 0.5 cm width, and the modulus at 100%, the maximum strength, and the maximum elongation thereof were measured under the conditions of chuck interval of 2 cm and tensile speed of 200 mm/min, using Autocom Type C universal tester (manufactured by Key SE Corporation), in a constant temperature and humidity chamber controlled to 23° C. and 50% RH.

<Liquid Physical Properties>
[Blending Stability]

The resulting aqueous dispersion was mixed to a solids content of 5% by weight, ethanol content of 10% by weight, and 1,3-butanediol content of 5% by weight (the balance is water), and the mixture was allowed to stand at room temperature. The state of the resulting liquid after one week was evaluated visually.

◎: No change is observed.

○: Some change in viscosity is observed for a certain period of time after mixing, but the viscosity is stabilized afterwards.

Δ: Some concentration gradient, precipitation, generation of aggregates, and change in viscosity are observed.

x: Obvious concentration gradient, precipitation, and generation of aggregates are observed.

[Pigment Dispersibility]

To a sample liquid prepared for the blending stability test, 1% by weight (excluded number) of carbon black pigment was added, followed by stirring at 1,200 rpm for 5 minutes using a disper. The properties of the resulting sample liquid containing the pigment was evaluated visually.

○: Pigment particles are stably dispersed to form a uniform liquid.

Δ: A portion of the pigment particles are aggregated.

x: Entire system is aggregated.

<Applied Physical Properties>
[C. R.: Curl Retention]

C. R. When the Resin Alone is Used

The sample is coated on a hair sample, and the coated hair sample is curled and dried in that state. After leaving the sample to stand for 3 hours under the following predetermined temperature and the humidity conditions, the level of the curl retention is observed.

As the sample liquid, the obtained aqueous solution was diluted with water to a solids content of 30% by weight, and the resultant was coated on a hair bundle having a length of 23 cm and weight of 2 g, such that the coated amount would be 0.7 g. The hair bundle was then curled around a cold rod having a diameter of 1 cm, dried at 50° C. for 2 hours, removed from the rod, and suspended in an environment of 30° C. and 90% RH. Three hours later, the length of the curled hair bundle was measured, and the curl retention rate was calculated according to the following equation.

Curl retention rate (%)=(23-"length after 3 hours")×100/(23-"initial length")

It should be noted, however, the "length" refers to the length of the hair bundle in a curled state.

C. R. When 1,3BG (1,3-Butanediol) is Blended to the Resin

The C. R. was evaluated in the same manner as described in the above mentioned "C. R. when the resin alone is used", except that the sample liquid was diluted to a solids content of 5% by weight, and a 1,3-butanediol content of 5% by weight, with the balance being water.

<Sensory Evaluation>
[Elasticity of Curled Hair Bundle]

A hair bundle was prepared in the same manner as described in the above mentioned "C. R. when the resin alone is used" under the section of [C. R.: Curl retention], and then the hair bundle was grasped in a hand to evaluate its texture. The evaluation was carried out based on the following standards.

◎: The hair feels soft and elastic.

○: The hair feels elastic, but there is a feeling of stiffness or insufficient tension, as compared to those evaluated as "◎"

x: The hair feels hard or too soft.

[Glossiness of Curled Hair Bundle]

A hair bundle was prepared in the same manner as described in the "C. R. when the resin alone is used" under the section of [C. R.: Curl retention]. The obtained hair bundle was visually compared with a standard curled hair bundle, which was prepared using water as a sample liquid, and the level of the glossiness was evaluated according to the following standards.

○: Glossier than the standard sample.

Δ: Approximately as glossy as the standard sample.

x: Less glossy than the standard sample.

<Reference>
[C. R.: (Resin Alone)—(1,3BG Blended)]

The difference between the numerical value of the curl retention rate when the resin alone was used, and the numerical value of the curl retention rate when 1,3-BG was blended to the resin was calculated, and the evaluation thereof was carried out.

It should be noted that, the lower the value (the value closer to "0"), the better. When the obtained value is "0", it means that the curl retention rate does not change due to the addition of 1,3BG, which is an organic solvent. If that is the case, the resin "has the 1,3BG resistance".

[Difference Between Mwp of A and B]

The difference between the peak molecular weight (Mwp) of the component (A) and the peak molecular weight (Mwp) of the component (B), ((Mwp of B)−(Mwp of A)), was calculated.

As described above, the difference between the two is preferably about 20 or more and 200 or less.

Examples 1-1 to 1-14 and Comparative Examples 1-1 to 1-4

In each of Examples and Comparative examples, to a four-necked flask equipped with a thermometer, a stirring device and a reflux condenser, the specified amounts of components listed in the section of the Urethane, the Polymerization inhibitor, and the Acrylic component, under the Pre-emulsion in Table 1, were added, followed by mixing at an internal temperature of 50° C. Then the temperature was raised to 90° C., and the resultant was allowed to react for 5 hours at this temperature to obtain a carboxyl group-containing polyurethane (A) containing an isocyanate group and a carboxyl group.

Next, while maintaining the liquid temperature at 50° C., the basic compound listed in the section of the Neutralizer in Table 1 was added in the specified amount (the amount corresponding to 1 equivalent with respect to the amount of carboxyl groups contained in the component (A)), to neutralize all of the carboxyl groups contained in the carboxyl group-containing polyurethane (A). Note that, the degree of neutralization is 100% at this time.

Next, the aqueous medium (deionized water: DW) shown in the section of the Emulsification under the Pre-emulsion in Table 1 was dropped to the resulting solution, at 50° C. over 15 minutes, to obtain a milk white, transparent dispersion liquid.

The resulting dispersion liquid was maintained at 50° C., and at this temperature, the polymerization initiator and the reducing agent listed in the section of the Polymerization step in Table 1 were added in the respective specified amounts, to initiate the polymerization of the polymerizable monomers. After the generation of exothermic heat has completed, the temperature of the resultant was further increased to 70° C., and maintained at that temperature for 3 hours. Thus, an aqueous emulsion containing an urethane-(meth)acrylic composite resin and unreacted polymerizable monomers (B) was obtained, for each of Examples and Comparative Examples.

The abovementioned measurements and evaluations were carried out for each of the resulting aqueous emulsions. The results are shown in Tables 1 and 2. Further, a graph showing the weight average molecular weight (Mw) and the like measured in Example 1-2 is shown in FIG. 1.

TABLE 1

| | | | | | | Examples | | | | |
|---|---|---|---|---|---|---|---|---|---|---|
| | | | | | | 1-1 | 1-2 | 1-3 | 1-4 | 1-5 |
| Aqueous dispersion | Pre-emulsion | Urethane (Component A) | D2000 | | (parts by weight) | 39.11 | 21.66 | 39.11 | 39.11 | 21.66 |
| | | | D1000 | | (parts by weight) | 9.83 | 21.78 | 9.83 | 9.83 | 21.78 |
| | | | PTMG2000 | | (parts by weight) | — | — | — | — | — |
| | | | PTMG1000 | | (parts by weight) | — | — | — | — | — |
| | | | PTMG650 | | (parts by weight) | — | — | — | — | — |
| | | | PEG1000 | | (parts by weight) | — | — | — | — | — |
| | | | N4073 | | (parts by weight) | — | — | — | — | — |
| | | | Bis-MPA | | (parts by weight) | 7.83 | 8.67 | 7.83 | 7.83 | 8.67 |
| | | | IPDI | | (parts by weight) | 43.23 | 47.88 | 43.23 | 43.23 | 47.88 |
| | | | Tg | Lower temperature side | (°C.) | −40 | −17 | −40 | −40 | −17 |
| | | | | Higher temperature side | (°C.) | 80 | 80 | 80 | 80 | 80 |
| | | | Acid value | | (mg KOH/g) | 32.7 | 36.3 | 32.7 | 32.7 | 36.3 |
| | | Polymerization inhibitor | MEHQ | | (parts by weight) | 0.015 | 0.015 | 0.015 | 0.015 | 0.015 |
| | | Acrylic component (Component B) | MMA | | (parts by weight) | 85 | 85 | 100 | 100 | 100 |
| | | | BA | | (parts by weight) | 15 | 15 | 0 | 0 | 0 |
| | | | Tg | | (°C.) | 68.6 | 68.6 | 105 | 105 | 105 |
| | | Neutralizer | 10% KOH aq. | | (parts by weight) | — | — | — | 32.74 | — |
| | | | Triethanolamine | | (parts by weight) | 8.69 | 9.63 | 8.69 | — | 9.63 |
| | | Emulsification | DW | | (parts by weight) | 281.08 | 278.44 | 281.08 | 243.06 | 278.44 |
| | Polymerization step | Initiator | tBPO | | (parts by weight) | 5 | 5 | 5 | 0.5 | 0.5 |
| | | Reducing agent | AsA | | (parts by weight) | 25 | 25 | 25 | 0.25 | 0.25 |
| | U/A composite resin | Ratio: Component A/Component B | | | (weight ratio) | 50/50 | 50/50 | 50/50 | 50/50 | 50/50 |
| | | Mw | | | (×10⁴) | 67 | 68 | 41 | 41 | 68 |
| | | Mw/Mn | | | | 30 | 53 | 35 | 35 | 53 |
| | | Mwp | Component A | | (×10⁴) | 11.9 | 2.5 | 2.6 | 2.6 | 2.5 |
| | | | Component B | | (×10⁴) | 39 | 106 | 38 | 37 | 106 |
| | | Gel fraction | | | (% by weight) | 80 | 80 | 85 | 88 | 80 |
| | | MFT | | | (°C.) | 0 | 0 | 0 | 10 | 0 |
| Physical properties/ Evaluation | Physical properties of film | Dryness fraction | | | (%) | 31 | 34 | 28 | 36 | 33 |
| | | S-S 100% M | | | | 16.8 | 22.7 | 19.5 | — | 26.1 |
| | | S-S maximum strength | | | | 21 | 25 | 19.6 | 25.2 | 26.5 |
| | | S-S maximum elongation | | | | 310 | 184 | 125 | 12 | 130 |
| | Liquid physical properties | Blending stability | | | | ◎ | ◎ | ○ | ○ | ○ |
| | | Pigment dispersibility | | | | ○ | ○ | ○ | ○ | ○ |
| | Applied physical properties | C.R. (resin alone) | | | | 90 | 83 | 91 | 91 | 88 |
| | | C.R. (1,3BG blended) | | | | 83 | 80 | 87 | 87 | 80 |
| | Sensory evaluation | Elasticity of curled hair bundle | | | | ○ | ◎ | ◎ | ◎ | ◎ |
| | | Glossiness of curled hair bundle | | | | ○ | ○ | ○ | ○ | ○ |
| | Reference values | C.R. (resin alone) - (1.3BG blended) | | | | 7 | 3 | 4 | 4 | 8 |
| | | Difference in Mwp between A and B | | | (×10⁴) | 27 | 104 | 35 | 34 | 104 |

| | | | | | | Examples | | | |
|---|---|---|---|---|---|---|---|---|---|
| | | | | | | 1-6 | 1-7 | 1-8 | 1-9 |
| Aqueous dispersion | Pre-emulsion | Urethane (Component A) | D2000 | | (parts by weight) | 13 | 39.11 | 39.11 | — |
| | | | D1000 | | (parts by weight) | 13.07 | 9.83 | 9.83 | — |
| | | | PTMG2000 | | (parts by weight) | — | — | — | 50.81 |
| | | | PTMG1000 | | (parts by weight) | — | — | — | 1.82 |
| | | | PTMG650 | | (parts by weight) | — | — | — | — |
| | | | PEG1000 | | (parts by weight) | — | — | — | — |
| | | | N4073 | | (parts by weight) | — | — | — | — |
| | | | Bis-MPA | | (parts by weight) | 5.2 | 7.83 | 7.83 | 7.13 |
| | | | IPDI | | (parts by weight) | 28.73 | 43.23 | 43.23 | 39.39 |
| | | | Tg | Lower temperature side | (°C.) | −17 | −40 | −40 | −50 |
| | | | | Higher temperature side | (°C.) | 80 | 80 | 80 | 140 |
| | | | Acid value | | (mg KOH/g) | 36.3 | 32.7 | 32.7 | 30.4 |
| | | Polymerization inhibitor | MEHQ | | (parts by weight) | 0.015 | 0.015 | 0.015 | 0.015 |
| | | Acrylic component (Component B) | MMA | | (parts by weight) | 40 | 50 | 70 | 50 |
| | | | BA | | (parts by weight) | 0 | 50 | 30 | 50 |
| | | | Tg | | (°C.) | 105 | 6 | 38.6 | 6 |

TABLE 1-continued

|  |  |  |  |  |  |  |  |  |
|---|---|---|---|---|---|---|---|---|
|  |  | Neutralizer | 10% KOH aq. | (parts by weight) | — | 32.74 | 32.74 | 29.84 |
|  |  |  | Triethanolamine | (parts by weight) | 5.78 | — | — | — |
|  |  | Emulsification | DW | (parts by weight) | 138.13 | 243.06 | 243.06 | 231.81 |
|  | Polymerization | Initiator | tBPO | (parts by weight) | 0.3 | 0.5 | 0.5 | 0.5 |
|  | step | Reducing agent | AsA | (parts by weight) | 0.15 | 0.25 | 0.25 | 0.25 |
|  | U/A composite | Ratio: Component A/Component B | (weight ratio) |  | 60/40 | 50/50 | 50/50 | 50/50 |
|  | resin | Mw |  | ($\times 10^4$) | 68 | 22 | 41 | 48 |
|  |  | Mw/Mn |  |  | 53 | 22 | 35 | 33 |
|  |  | Mwp | Component A | ($\times 10^4$) | 2.0 | 4.0 | 2.6 | 8.9 |
|  |  |  | Component B | ($\times 10^4$) | 106 | 71 | 38 | 130 |
|  |  | Gel fraction |  | (% by weight) | 78 | 91 | 80 | 85 |
|  |  | MFT |  | (° C.) | 0 | 0 | 0 | 0 |
| Physical | Physical | Dryness fraction |  | (%) | 32 | 25 | 37 | 33 |
| properties/ | properties | S-S 100% M |  |  | 10.6 | 6.3 | 8.4 | 22.5 |
| Evaluation | of film | S-S maximum strength |  |  | 22.7 | 19.9 | 15.6 | 29.2 |
|  |  | S-S maximum elongation |  |  | 520 | 930 | 635 | 300 |
|  | Liquid | Blending stability |  |  | ○ | ○ | ○ | ◎ |
|  | physical | Pigment dispersibility |  |  | ○ | ○ | ○ | ○ |
|  | properties |  |  |  |  |  |  |  |
|  | Applied | C.R. (resin alone) |  |  | 90 | 95 | 80 | 91 |
|  | physical | C.R. (1,3BG blended) |  |  | 83 | 90 | 73 | 87 |
|  | properties |  |  |  |  |  |  |  |
|  | Sensory | Elasticity of curled hair bundle |  |  | ◎ | ◎ | ◎ | ○ |
|  | evaluation | Glossiness of curled hair bundle |  |  | ○ | ○ | ○ | ○ |
|  | Reference | C.R. (resin alone) - (1.3BG blended) |  |  | 7 | 5 | 7 | 4 |
|  | values | Difference in Mwp between A and B | ($\times 10^4$) |  | 104 | 67 | 35 | 121 |

TABLE 2

|  |  |  |  |  |  | Examples |  |  |  |  |
|---|---|---|---|---|---|---|---|---|---|---|
|  |  |  |  |  |  | 1-10 | 1-11 | 1-12 | 1-13 | 1-14 |
| Aqueous | Pre-emulsion | Urethane | D2000 |  | (parts by weight) | 47.25 | 11.96 | 2.26 | — | 44.34 |
| dispersion |  | (Component A) | D1000 |  | (parts by weight) | — | 30.07 | 45.35 | — | 2.23 |
|  |  |  | PTMG2000 |  | (parts by weight) | — | — | — | 53.64 | — |
|  |  |  | PTMG1000 |  | (parts by weight) | — | — | — | — | — |
|  |  |  | PTMG650 |  | (parts by weight) | — | — | — | 0.59 | — |
|  |  |  | PEG1000 |  | (parts by weight) | 4.75 | — | — | — | — |
|  |  |  | N4073 |  | (parts by weight) | — | — | — | — | — |
|  |  |  | Bis-MPA |  | (parts by weight) | 8.32 | 11.17 | 8.28 | 8.15 | 10.06 |
|  |  |  | IPDI |  | (parts by weight) | 39.68 | 46.8 | 44.12 | 37.62 | 43.37 |
|  |  |  | Tg | Lower temperature side | (° C.) | -40 | -17 | -17 | -50 | -40 |
|  |  |  |  | Higher temperature side | (° C.) | 80 | 80 | 70 | 140 | 80 |
|  |  |  | Acid value |  | (mg KOH/g) | 34.8 | 46.7 | 34.6 | 34.1 | 42.1 |
|  |  | Polymerization inhibitor | MEHQ |  | (parts by weight) | 0.015 | 0.015 | 0.015 | 0.015 | 0.015 |
|  |  | Acrylic | MMA |  | (parts by weight) | 50 | 68 | 50 | 40 | 10 |
|  |  | component(Com- | BA |  | (parts by weight) | 50 | 32 | 50 | 60 | 90 |
|  |  | ponent B) | Tg |  | (° C.) | 6 | 35 | 6 | -2 | -40 |
|  |  | Neutralizer | 10% KOH aq. |  | (parts by weight) | 34.8 | 46.72 | — | 34.06 | 42.06 |
|  |  |  | Triethanolamine |  | (parts by weight) | — | — | 9.19 | — | — |
|  |  | Emulsification | DW |  | (parts by weight) | 236.89 | 252.11 | 309.5 | 232.08 | 258.49 |
|  | Polymerization | Initiator | tBPO |  | (parts by weight) | 0.5 | 0.5 | 0.5 | 0.5 | 0.5 |
|  | step | Reducing agent | AsA |  | (parts by weight) | 0.25 | 0.25 | 0.25 | 0.25 | 0.25 |
|  | U/A composite | Ratio: Component A/Component B |  |  | (weight ratio) | 50/50 | 50/50 | 50/50 | 50/50 | 50/50 |
|  | resin | Mw |  |  | ($\times 10^4$) | 69 | 24 | 24 | 48 | 69 |
|  |  | Mw/Mn |  |  |  | 36 | 23 | 24 | 33 | 36 |
|  |  | Mwp | Component A |  | ($\times 10^4$) | 3.7 | 2.4 | 2.5 | 8.8 | 3.7 |
|  |  |  | Component B |  | ($\times 10^4$) | 105 | 30 | 30 | 130 | 104 |
|  |  | Gel fraction |  |  | (% by weight) | 78 | 90 | 91 | 88 | 77 |
|  |  | MFT |  |  | (° C.) | 0 | 5 | 0 | 0 | 0 |
| Physical | Physical | Dryness fraction |  |  | (%) | 25 | 33 | 35 | 33 | 30 |
| properties/ | properties | S-S 100% M |  |  |  | 5 | — | 9.3 | 7.4 | 4.1 |
| Evaluation | of film | S-S maximum strength |  |  |  | 22 | 25 | 27.1 | 24.6 | 15.6 |
|  |  | S-S maximum elongation |  |  |  | 985 | 11 | 715 | 650 | 1200 |
|  | Liquid | Blending stability |  |  |  | ○ | ○ | ○ | ◎ | ○ |
|  | physical | Pigment dispersibility |  |  |  | ○ | ◎ | ◎ | ○ | ○ |
|  | properties |  |  |  |  |  |  |  |  |  |
|  | Applied | C.R. (resin alone) |  |  |  | 90 | 80 | 85 | 83 | 78 |
|  | physical | C.R. (1,3BG blended) |  |  |  | 88 | 88 | 90 | 85 | 80 |
|  | properties |  |  |  |  |  |  |  |  |  |

TABLE 2-continued

|  |  |  |  |  |  |  |  |  |
|---|---|---|---|---|---|---|---|---|
| Sensory evaluation | Elasticity of curled hair bundle | | | | ◎ | ◎ | ◎ | ○ | ◎ |
| | Glossiness of curled hair bundle | | | | ○ | ○ | ○ | ○ | ○ |
| Reference values | C.R. (resin alone) - (1.3BG blended) | | | | 2 | −8 | −5 | −2 | −2 |
| | Difference in Mwp between A and B | | (×10⁴) | | 101 | 28 | 28 | 121 | 100 |

| | | | | | Comparative Examples | | | |
|---|---|---|---|---|---|---|---|---|
| | | | | | 1-1 | 1-2 | 1-3 | 1-4 |
| Aqueous dispersion | Pre-emulsion | Urethane (Component A) | D2000 | (parts by weight) | 53.47 | — | 39.11 | 21.66 |
| | | | D1000 | (parts by weight) | — | — | 9.83 | 21.78 |
| | | | PTMG2000 | (parts by weight) | — | — | — | — |
| | | | PTMG1000 | (parts by weight) | — | — | — | — |
| | | | PTMG650 | (parts by weight) | | | | |
| | | | PEG1000 | (parts by weight) | | | | |
| | | | N4073 | (parts by weight) | — | 52.34 | — | — |
| | | | Bis-MPA | (parts by weight) | 7.13 | 7.31 | 7.83 | 8.67 |
| | | | IPDI | (parts by weight) | 39.39 | 40.36 | 43.23 | 47.88 |
| | | | Tg Lower temperature side | (° C.) | −40 | 0 | −40 | −17 |
| | | | Higher temperature side | (° C.) | 80 | 160 | 80 | 80 |
| | | | Acid value | (mg KOH/g) | 29.8 | 30.6 | 32.7 | 36.3 |
| | | Polymerization inhibitor | MEHQ | (parts by weight) | 0.015 | 0.015 | — | — |
| | | Acrylic component (Component B) | MMA | (parts by weight) | 50 | 100 | — | — |
| | | | BA | (parts by weight) | 50 | 0 | — | — |
| | | | Tg | (° C.) | 6 | 105 | | |
| | | Neutralizer | 10% KOH aq. | (parts by weight) | 29.84 | 30.57 | 32.74 | — |
| | | | Triethanolamine | (parts by weight) | — | — | — | 9.63 |
| | | Emulsification | DW | (parts by weight) | 241.47 | 241.68 | 243.06 | 278.44 |
| | Polymerization step | Initiator | tBPO | (parts by weight) | 0.5 | 0.5 | — | — |
| | | Reducing agent | AsA | (parts by weight) | 0.25 | 0.25 | — | — |
| | U/A composite resin | Ratio: Component A/Component B | | (weight ratio) | 50/50 | 50/50 | 100/0 | 100/0 |
| | | Mw | | (×10⁴) | 14 | 26 | — | — |
| | | Mw/Mn | | | 19 | 19 | — | — |
| | | Mwp | Component A | (×10⁴) | 5.4 | 2.7 | 5.4 | 2.5 |
| | | | Component B | (×10⁴) | 16 | 57 | — | — |
| | | Gel fraction | | (% by weight) | 60 | 88 | — | — |
| | | MFT | | (° C.) | 0 | 50 | 0 | 0 |
| Physical properties/ Evaluation | Physical properties of film | Dryness fraction | | (%) | 33 | 30 | 25 | 15 |
| | | S-S 100% M | | | 4.6 | 20.2 | 9.5 | 3.1 |
| | | S-S maximum strength | | | 15 | 28.5 | 33.3 | 23.2 |
| | | S-S maximum elongation | | | 900 | 335 | 1100 | 1450 |
| | Liquid physical properties | Blending stability | | | Δ | ○ | X | X |
| | | Pigment dispersibility | | | Δ | Δ | Δ | Δ |
| | Applied physical properties | C.R. (resin alone) | | | 84 | 80 | 95 | 73 |
| | | C.R. (1,3BG blended) | | | 70 | 90 | 80 | 55 |
| | Sensory evaluation | Elasticity of curled hair bundle | | | ○ | X | X | X |
| | | Glossiness of curled hair bundle | | | Δ | X | X | X |
| | Reference values | C.R. (resin alone) - (1.3BG blended) | | | 14 | −10 | 15 | 18 |
| | | Difference in Mwp between A and B | | (×10⁴) | 11 | 54 | — | — |

<Polyurethane and U/A Resin or Aqueous Dispersion of U/A Resin According to the Second Invention>

Next, Examples of the polyurethane and the U/A resin or the aqueous dispersion of the U/A resin according to the second invention will be described.

<<1. Raw Materials>>

<Polyol Units>

N4073 Trade name: NIPPOLLAN 4073, a polyester polyol of 1,6-hexanediol and adipic acid (1,6HD-AA), number average molecular weight (Mn)=2,000; manufactured by Nippon Polyurethane Industry Co., Ltd.

P-2012 Trade name: Kuraray Polyol P-2012, a mixed polyester polyol of methylpentanediol and adipic acid/isophthalic acid (MPD-AA-IP) (molar ratio of adipic acid/isophthalic acid=1/1), number average molecular weight (Mn)=2,000; manufactured by Kuraray Co., Ltd.

P-1030 Trade name: Kuraray Polyol P-1030, a polyester polyol of methylpentanediol and isophthalic acid (MPD-IP), number average molecular weight (Mn)=1,000; manufactured by Kuraray Co., Ltd.

P-2030 Trade name: Kuraray Polyol P-2030, a polyester polyol of methylpentanediol and isophthalic acid, number average molecular weight (Mn)=2,000; manufactured by Kuraray Co., Ltd.

<Carboxyl Group-Containing Polyvalent Hydroxy Compound>

DMPA Dimethylolpropionic acid (carboxylic acid-containing polyol); manufactured by Perstorp Japan Co., Ltd.

<Polyvalent Isocyanate Compound, Polymerization Inhibitor, Polymerizable Monomer, Radical Polymerization Initiator, Reducing Agent, and Basic Compound>

As the polyvalent isocyanate compound, polymerization inhibitor, polymerizable monomer, radical polymerization initiator, reducing agent, and basic compound, the same as those described in Examples in the <Polyurethane and U/A resin or aqueous dispersion of U/A resin according to the first invention> section were used.

(Evaluation Methods)

[Oil Resistance]

A solution prepared by mixing a silicone oil (KF-995; manufactured by Shin-Etsu Chemical Co., Ltd.) and the polyurethane or the U/A resin at a weight ratio of 50/50 is cast at 23° C., onto a plate made of a polypropylene resin. After allowing the resultant to stand for 6 hours, a portion of the resulting film is picked up using forceps, and the state of the film formation is observed.

⊚: The formed thin film can be stably picked up by forceps.

○: The formed thin film can be picked up by forceps without rupturing, while it is being picked up.

Δ: Although a film is formed on the resin sheet, when picked up by forceps, the film ruptures while it is being picked up.

x: A film is not formed.

[Mechanical Stability]

Using a paint shaker (Model 5400-H3) manufactured by RED DEVIL corporation, 15 parts by weight of pigment (Pigment Blue 15 (trade name), manufactured by Tokyo Chemical Industry Co., Ltd.), 20 parts by weight (in terms of solids content) of polymer (the polyurethane or the aqueous dispersion of the U/A resin according to the present invention), isopropanol (first grade reagent, manufactured by Wako Pure Chemical Industries, Ltd.), and ion exchanged water were added to a total blended amount of 100 parts by weight. The resulting mixed solution was stirred and mixed for 1 hour, followed by filtering using a 100 mesh-Nylon net. Then the residue remaining on the net was visually observed.

⊚: No or little residue is observed.

○: The Nylon mesh appears as if it is lightly colored due to the residue remaining on the mesh net, but there is no problem in the filterability.

Δ: The Nylon mesh is covered with a heavy residue, resulting in a poor filterability.

x: Entire solution is gelated and unable to be filtered.

[Pigment Dispersibility]

A blended solution containing the U/A resin which was prepared for the evaluation of the mechanical stability was coated on a glass plate using a bar (No. 4), and dried at room temperature for 30 minutes. Then the coated surface was observed, and the evaluation was carried out according to the following standards.

⊚: The coated surface is glossy and has a uniform color.

○: Although inferior to those evaluated as "⊚", the coated surface is glossy and has a uniform color.

Δ: The coated surface is even, but has irregularities in color.

x: The coated surface is uneven, and/or has significant irregularities in color.

(Evaluation of Urethane-(Meth)Acrylic Composite Resin)

The evaluation of the [Glass transition temperature (Tg) of component (A) and component (B)], [Weight average molecular weight and molecular weight distribution of component (A)], [Weight average molecular weight and molecular weight distribution of U/A resin], [Gel fraction], [Stress-strain (S-S) (Maximum strength and maximum elongation)], [Blending stability], and [C. R.: Curl retention] of the urethane-(meth)acrylic composite resin or the aqueous dispersion thereof were carried out in the same manner as those described in Examples in the <Polyurethane and U/A resin or aqueous dispersion of U/A resin according to the first invention> section.

Examples 2-1, 2-2, and Comparative Example 2-2: Production of Urethane

In each of Examples and Comparative examples, to a four-necked flask equipped with a thermometer, a stirring device and a reflux condenser, the specified amounts of the raw materials for the urethane and the reaction solvent shown in Table 3 were added, followed by mixing at an internal temperature of 50° C. Then the temperature was raised to 90° C., and the resultant was allowed to react for 5 hours at this temperature to obtain a carboxyl group-containing urethane prepolymer containing an isocyanate group and a carboxyl group.

Thereafter, the specified amount of the neutralizer (basic compound) shown in Table 3 was added while maintaining the liquid temperature at 50° C., to neutralize all or a portion of the carboxyl groups contained in the carboxyl group-containing urethane prepolymer.

To the resultant, the phase inversion water (deionized water: DW) was dropped in the amount shown in Table 3 over 15 minutes, while maintaining the internal temperature at 50° C., to carry out the phase inversion of the emulsion, thereby obtaining a milk white, transparent dispersion liquid.

The temperature of the resulting dispersion liquid was then raised to 80° C., and the reaction solvent (methyl ethyl ketone (MEK), ethanol (EtOH)) used in the production of the urethane prepolymer was collected. Thus, a polyurethane dispersion liquid (dispersion) was obtained, for each of Examples and Comparative Examples.

The content of the isophthalic acid unit in the above mentioned Example 2-1, which is calculated according to the above description, is as follows.

In the "P-1030" described above, the acid component is isophthalic acid alone, the diol component is methylpentanediol alone, and the molecular weight (PEsPO) is 1,000.

Based on the above, the PA unit formula weight is 148, the DOL unit formula weight is 100, and the molecular weight of terminal diol is 101, and therefore, the PA unit content in the polyurethane can be calculated as follows.

1) PA unit number $$\text{PA unit number (NumberPA)} = (1{,}000 - 101)/(100 + 148) = 4 \text{ (rounded to an integer)}$$

2) Based on the above 1), the isophthalic acid unit content (wtPA) in PEsPO can be calculated as follows.

$$wtPA = (NumberPA) \times PA \text{ unit formula}$$
$$\text{weight}/(PA \text{ unit formula weight} + DOL \text{ unit formula weight}) =$$
$$4 \times 148/1{,}000 = 0.59$$

3) The PA unit content during the charging can be calculated, from the above mentioned results and from the "Charged amount of the polyol" (0.23) shown in Table 3, according to the following equation.

$$\text{PA unit content during the charging} = 0.23 \times 0.59 = 0.14$$

4) The content percentage of the isophthalic acid unit contained in the polyurethane can be calculated from the above mentioned results and the charged amount of each of the components shown in Table 3 as the raw materials for the urethane, according to the following equation.

PA unit content (wt %)=(0.23×059)/(60.8+0.2+7.8+ 31.2)×100=0.1% by weight

This value corresponds to the "Isophthalic acid (IP) content (wt %) in polyurethane" in Table 3.

In Examples 2 to 6, 8, and 9, and Comparative Example 1, in which P-1030 is used as the diol component, the PA unit content in the polyurethane can be calculated in the same manner.

Examples 2-3 to 2-8, and Comparative Example 2-3: Production of U/A Resin

In each of Examples and Comparative examples, to a four-necked flask equipped with a thermometer, a stirring device and a reflux condenser, the specified amounts of the raw materials for the urethane, the raw materials for the acrylic component and the polymerization inhibitor shown in Table 3 were added, followed by mixing at an internal temperature of 50° C. Then the temperature was raised to 90° C., and the resultant was allowed to react for 5 hours at this temperature, to obtain a carboxyl group-containing urethane prepolymer containing an isocyanate group and a carboxyl group, dispersed in (meth)acrylic polymerizable monomers.

Then the specified amount of the neutralizer (basic compound) listed in Table 3 was added while maintaining the liquid temperature at 50° C., to neutralize all or a portion of the carboxyl groups contained in the carboxyl group-containing urethane prepolymer.

To the resultant, the phase inversion water (deionized water: DW) was dropped in the amount shown in Table 3 over 15 minutes, while maintaining the internal temperature at 50° C., to carry out the phase inversion of the emulsion, thereby obtaining a milk white, transparent dispersion liquid.

While maintaining the temperature of the dispersion liquid at 50° C., the specified amounts of the catalysts for polymerization of the acrylic component (the polymerization initiator and the reducing agent) shown in Table 3 were added, to initiate the polymerization of the (meth)acrylic polymerizable monomers. After the generation of exothermic heat due to polymerization has completed, the temperature of the resultant was further raised to 70° C., and maintained for 3 hours at that temperature. Thus, an aqueous dispersion of an urethane-(meth)acrylic composite resin containing an urethane-(meth)acrylic composite resin and unreacted polymerizable monomers was obtained, for each of Examples and Comparative Examples.

In the above mentioned Example 2-7, P-2012, which is a mixed polyester polyol of adipic acid and isophthalic acid (the diol component is methylpentanediol alone), is used as the polyol, which is the raw material of the urethane. In this case, the "PA unit content in polyurethane" can be calculated as follows.

1) The formula weights of the dicarboxylic acids used, each multiplied by each usage ratio thereof (molar fraction), were totaled to obtain the "average formula weight of dicarboxylic acids", and using this average formula weight, the "dicarboxylic acid unit number" which corresponds to the "NumberPA" when only one dicarboxylic acid is used, is calculated.

The molecular weight, molar fraction and the like of the P-2012 and the raw materials thereof, are as follows.

P-2012: molecular weight of PEsPO=2,000, molecular weight of terminal DOL=101
Methylpentanediol: formula weight of DOL unit=100
Adipic acid: formula weight of adipic acid unit=128, molar fraction=0.5
Isophthalic acid: formula weight of PA unit=148, molar fraction=0.5
Based on the above, Average formula weight of dicarboxylic acids= (128×0.5)+(148×0.5)=138

Dicarboxylic acid unit number=(2,000−101)/ (100+138)=8 (rounded to an integer)

2) Based on the above results, the dicarboxylic acid unit content in the PEsPO is calculated as follows.

Dicarboxylic acid unit content in PEsPO=7.98×138/ 2,000=0.55

3) Based on the charged amount of the PEsPO=54.52 (Table 3), the dicarboxylic acid unit content during the charging is calculated as follows.

Dicarboxylic acid unit content (%) during the charging=54.52×0.55=29.99

4) The dicarboxylic acid unit content in the polyurethane can be calculated, from the charged amount of the raw materials shown in Table 3, as follows.

Dicarboxylic acid unit content (wt %)=29.99/ (54.52+9.14+36.34)×100=29.99 wt %

5) Based on the above results, the PA unit content in the polyurethane is calculated from the PA unit formula weight and the molar fraction of PA.

PA unit content (wt %)=29.99×(148/138)×0.5= 16.08 wt %

This value is shown as the "IP content in polyurethane (wt %)" in Table 3.

Example 2-9: An Example in which the First and the Second Neutralization Steps were Carried Out The same procedures as in the above mentioned Examples 3 to 8 were carried out, except that the raw materials shown in Table 3 were used, to synthesize a carboxyl group-containing urethane prepolymer containing an isocyanate group and a carboxyl group. Thereafter, while maintaining the temperature of the resultant at 50° C., TEA (triethanolamine), of the neutralizers shown in Table 3, was used to neutralize one portion of the carboxyl groups contained in the carboxyl group-containing urethane prepolymer (the first neutralization step).

Then, phase inversion was carried out in the same manner as in Example 1, using the phase inversion water (deionized water: DW), to obtain a milk white, transparent dispersion liquid.

To the resulting dispersion liquid, the specified types and the amounts of the raw materials (monomers) for the acrylic component, the polymerization catalysts (the initiator and the reducing agent), and the like, as shown in Table 3, were added. Then the resultant was subjected to polymerization and aging (raising and maintaining the temperature after the generation of exothermic heat due to polymerization has completed) in the same manner as in Examples 3 to 8, to obtain an aqueous dispersion of an urethane-(meth)acrylic composite resin containing the urethane-(meth)acrylic composite resin and unreacted polymerizable monomers.

After cooling the resulting aqueous dispersion to 30° C., the potassium hydroxide in the amount shown in Table 3 was used to carry out the second neutralization step, to neutralize one portion of the carboxyl groups contained in the urethane-(meth)acrylic composite resin, thereby preparing an aqueous dispersion of the U/A resin.

Comparative Example 2-1

The same procedure as in Example 1 was carried out, except that the specified amounts of the raw materials for the urethane shown in Table 3 were used, and that MEK was used as the reaction solvent in the amount shown in Table 3, to obtain a carboxyl group-containing urethane prepolymer containing an isocyanate group and a carboxyl group.

Then the specified amount of ethanol (EtOH) shown in the section of the Reaction solvent in Table 3 was dropped at 50° C. for 15 minutes, to obtain a transparent solution.

The above mentioned measurements and evaluations of the resulting aqueous emulsions (the MEK/ethanol solution, in Comparative Example 2-1) were then carried out. The results are also shown in Table 3.

TABLE 3

| | | | | | | Examples | | | | | | |
|---|---|---|---|---|---|---|---|---|---|---|---|---|
| | | | | | | 2-1 | 2-2 | 2-3 | 2-4 | 2-5 | 2-6 | 2-7 |
| Polyurethane | Raw materials for urethane component | Polyols | N4073 | | (% by weight) | 60.77 | 47.56 | 60.77 | 47.56 | 22.21 | 18.74 | — |
| | | | P-2012 | | (% by weight) | — | — | — | — | — | — | 54.52 |
| | | | P-1030 | | (% by weight) | 0.23 | 1.52 | 0.23 | 1.52 | 22.21 | 37.48 | — |
| | | Dispersing group | DMPA | | (% by weight) | 7.84 | 10.45 | 7.84 | 10.45 | 11.17 | 6.29 | 9.14 |
| | | Diisocyanate | IPDI | | (% by weight) | 31.16 | 40.47 | 31.16 | 40.47 | 44.41 | 37.48 | 36.34 |
| | Residual NCO content | | | | (% by weight) | 2.12 | 3.31 | 2.12 | 3.31 | 3.50 | 3.15 | 2.86 |
| | Residual NCO | | | | (mol) | 0.10 | 0.16 | 0.10 | 0.16 | 0.17 | 0.15 | 0.14 |
| | Acid value | | | | (mg KOH/g) | 32.60 | 43.71 | 32.60 | 43.71 | 46.72 | 26.29 | 38.23 |
| | IP content in polyurethane | | | | (% by weight) | 0.14 | 0.90 | 0.14 | 0.90 | 13.10 | 22.12 | 16.08 |
| Acrylic component | Raw materials for acrylic component | Polymerizable monomers | MMA | | (% by weight) | — | — | 50.00 | 75.00 | 50.00 | 50.00 | 50.00 |
| | | | BA | | (% by weight) | — | — | 50.00 | 25.00 | 50.00 | 50.00 | 50.00 |
| | | Polymerization inhibitor | MEHQ | | (% by weight) | — | — | 0.02 | 0.02 | 0.02 | 0.02 | 0.02 |
| | Reaction solvent | | EtOH | | (% by weight) | — | — | — | — | — | — | — |
| | | | MEK | | (% by weight) | 100.00 | 100.00 | — | — | — | — | — |
| | Neutralizer | | KOH | | (% by weight) | 3.26 | 4.37 | 3.26 | 4.37 | 4.67 | 2.63 | 3.82 |
| | | | TEA | | (% by weight) | — | — | — | — | — | — | — |
| | Phase inversion water | | DW | | (% by weight) | 240.12 | 231.57 | 240.12 | 231.59 | 229.29 | 244.96 | 235.80 |
| | Catalysts for polymerization of acrylic components | Initiator | tBPO | | (% by weight) | — | — | 0.71 | 0.71 | 0.71 | 0.71 | 0.71 |
| | | Reducing agent | AsA | | (% by weight) | — | — | 0.30 | 0.25 | 0.30 | 0.25 | 0.25 |
| U/A resin | Mw | | | | ($\times 10^4$) | — | — | 27 | 40 | 30 | 28 | 44 |
| | Mw/Mn | | | | | — | — | 20 | 29 | 20 | 32 | 48 |
| | Mwp of urethane component | | | | ($\times 10^4$) | 4.4 | 4.8 | 4.3 | 4.7 | 4.6 | 5.6 | 12.3 |
| | Mwp of acrylic component | | | | ($\times 10^4$) | — | — | 49.7 | 86.6 | 58.6 | 32.3 | 75.6 |
| | Gel fraction | | | | (% by weight) | 64 | 35 | 72 | 33 | 71 | 98 | 90 |
| Physical properties/ Evaluation | Applied physical properties | C.R. | | | (resin alone) | 100 | 65 | 93 | 62 | 100 | 94 | 97 |
| | | | | | (1,3BG blended) | 97 | 95 | 97 | 94 | 100 | 90 | 100 |
| | | Blending stability | | | | ◯ | ◯ | ◎ | ◎ | ◎ | ◎ | ◎ |
| | | Oil resistance | | | | ◯ | ◎ | ◯ | ◎ | ◎ | ◎ | ◎ |
| | | Mechanical stability | | | | ◯ | ◯ | ◎ | ◯ | ◎ | ◎ | ◎ |
| | | Pigment dispersibility | | | | ◎ | ◯ | ◎ | ◯ | ◎ | ◯ | ◎ |
| | Physical properties of film | Maximum strength | | | (Mpa) | 29 | 15 | 22 | 13 | 20 | 26 | 26 |
| | | Maximum elongation | | | (%) | 620 | 10 | 670 | 6 | 275 | 60 | 520 |

| | | | | | | Examples | | Comparative Examples | | |
|---|---|---|---|---|---|---|---|---|---|---|
| | | | | | | 2-8 | 2-9 | 2-1 | 2-2 | 2-3 |
| Polyurethane | Raw materials for urethane component | Polyols | N4073 | | (% by weight) | 50.26 | 47.56 | 74.74 | 61.51 | 61.51 |
| | | | P-2012 | | (% by weight) | — | — | — | — | — |
| | | | P-1030 | | (% by weight) | 5.03 | 1.52 | 0.07 | — | — |
| | | Dispersing group | DMPA | | (% by weight) | 6.74 | 10.45 | 8.87 | 7.74 | 7.74 |
| | | Diisocyanate | IPDI | | (% by weight) | 37.97 | 40.47 | 16.32 | 30.75 | 30.76 |
| | Residual NCO content | | | | (% by weight) | 3.80 | 3.31 | 0.00 | 2.10 | 2.10 |
| | Residual NCO | | | | (mol) | 0.18 | 0.16 | 0.00 | 0.10 | 0.10 |
| | Acid value | | | | (mg KOH/g) | 28.20 | 43.71 | 39.63 | 32.35 | 32.35 |
| | IP content in polyurethane | | | | (% by weight) | 2.97 | 0.90 | 0.04 | 0.00 | 0.00 |
| Acrylic component | Raw materials for acrylic component | Polymerizable monomers | MMA | | (% by weight) | 50.00 | 75.00 | — | — | 75.00 |
| | | | BA | | (% by weight) | 50.00 | 25.00 | — | — | 25.00 |
| | | Polymerization inhibitor | MEHQ | | (% by weight) | 0.02 | 0.02 | — | — | 0.02 |
| | Reaction solvent | | EtOH | | (% by weight) | — | — | 50.00 | — | — |
| | | | MEK | | (% by weight) | — | — | 50.00 | 100.00 | — |

TABLE 3-continued

| | | | | | | | | | |
|---|---|---|---|---|---|---|---|---|---|
| | Neutralizer | | KOH | (% by weight) | 2.82 | 2.19 | — | 3.24 | 3.24 |
| | | | TEA | (% by weight) | — | 5.80 | — | — | — |
| | Phase inversion water | | DW | (% by weight) | 243.49 | 248.36 | — | 240.31 | 240.32 |
| | Catalysts for polymerization of acrylic components | Initiator | tBPO | (% by weight) | 0.71 | 0.71 | — | — | 0.71 |
| | | Reducing agent | AsA | (% by weight) | 0.25 | 0.25 | — | — | 0.25 |
| U/A resin | Mw | | | ($\times 10^4$) | 36 | 50 | — | — | 104 |
| | Mw/Mn | | | | 35 | 29 | — | — | 32 |
| | Mwp of urethane component | | | ($\times 10^4$) | 11.4 | 10.5 | 1.0 | 2.9 | 2.3 |
| | Mwp of acrylic component | | | ($\times 10^4$) | 49.1 | 43.2 | — | — | 104.0 |
| | Gel fraction | | | (% by weight) | 81 | 30 | 5 | 5 | 3 |
| Physical properties/ Evaluation | Applied physical properties | C.R. | | (resin alone) | 90 | 70 | 53 | 97 | 80 |
| | | | | (1,3BG blended) | 97 | 90 | 53 | 80 | 75 |
| | | Blending stability | | | ◎ | ◎ | X | Δ | ○ |
| | | Oil resistance | | | ◎ | ◎ | X | X | Δ |
| | | Mechanical stability | | | ◎ | ○ | Δ | Δ | X |
| | | Pigment dispersibility | | | ○ | ○ | Δ | Δ | Δ |
| | Physical properties of film | Maximum strength | | (Mpa) | 22 | 22 | 6 | 29 | 1.8 |
| | | Maximum elongation | | (%) | 460 | 12 | 5 | 590 | 5 |

Each of the polyurethanes or the U/A resins prepared in Examples 2-1 to 2-9 has a good oil resistance (film-forming ability from silicone oil), since it contains a specified amount of dicarboxylic acid unit(s) (phthalic acid-based unit, in particular).

On the other hand, those prepared in Comparative Examples exhibited a poor oil resistance, since each of the polyurethanes or the U/A resins contains no dicarboxylic acid unit, or contains the dicarboxylic acid unit in an amount less than the specified amount.

The invention claimed is:

1. An urethane-(meth)acrylic composite resin which is a composite resin obtained by complexing a polyurethane and a (meth)acrylic resin,
   wherein the polyurethane is obtained from a polyol component comprising a polyester polyol, and a polyvalent isocyanate component;
      wherein the polyester polyol comprises a structural unit derived from at least one dicarboxylic acid selected from the group consisting of phthalic acid, isophthalic acid and terephthalic acid; and
      wherein a content percentage of the structural unit derived from the dicarboxylic acid is 0.05% by weight or more and 50% by weight or less;
   wherein the composite resin has a weight average molecular weight (Mw) of one hundred thousand or more and two million or less, and a gel fraction of 20% by weight or more; and
   wherein the composite resin has a core-shell structure in which the polyurethane forms a shell portion and the (meth)acrylic resin forms a core portion,
   wherein the core-shell structure is formed by:
      preparing an emulsion by emulsifying and dispersing the polyurethane and a (meth)acrylic monomer as a raw material for the (meth)acrylic resin in an aqueous medium, and
      polymerizing the (meth)acrylic monomer, while the polyurethane undergoes a chain extension reaction, in the emulsion.

2. An urethane-(meth)acrylic composite resin which is a composite resin obtained by complexing a polyurethane and a (meth)acrylic resin,
   wherein the polyurethane is obtained from a polyol component comprising a polyester polyol, and a polyvalent isocyanate component;
      wherein the polyester polyol comprises a structural unit derived from at least one dicarboxylic acid selected from the group consisting of phthalic acid, isophthalic acid and terephthalic acid; and
   wherein the urethane-(meth)acrylic composite resin has a core-shell structure in which the polyurethane forms a shell portion and the (meth)acrylic resin forms a core portion, wherein the core-shell structure is formed by:
      preparing an emulsion by emulsifying and dispersing the polyurethane and a (meth)acrylic monomer as a raw material for the (meth)acrylic resin in an aqueous medium, and
      polymerizing the (meth)acrylic monomer, while the polyurethane undergoes a chain extension reaction, in the emulsion; and
   wherein the urethane-(meth)acrylic composite resin has a weight average molecular weight (Mw) of one hundred thousand or more and two million or less, and a gel fraction of 20% or more.

3. The urethane-(meth)acrylic composite resin according to claim 2, wherein the polyurethane constituting the composite resin is a polyurethane obtained from at least 2 polyol components and the polyvalent isocyanate component, and wherein polyol components each having a different number average molecular weight from each other and/or each comprising a different structural unit are used as the polyol components.

4. An aqueous dispersion of a urethane-(meth)acrylic composite resin, obtained by dispersing an urethane-(meth)acrylic composite resin according to (a) or (b) in an aqueous medium, the composite resin having a weight average molecular weight (Mw) of one hundred thousand and two million or less, and a gel fraction of 20% by weight or more:
   (a) an urethane-(meth)acrylic composite resin which is a composite resin obtained by complexing a polyurethane and a (meth)acrylic resin,
   wherein the polyurethane is obtained from a polyol component comprising a polyester polyol, and a polyvalent isocyanate component;
      wherein the polyester polyol comprises a structural unit derived from at least one dicarboxylic acid selected from the group consisting of phthalic acid, isophthalic acid and terephthalic acid;

wherein the polyurethane has a glass transition temperature (Tg) of −60° C. or more and 250° C. or less;

wherein the composite resin has a core-shell structure in which the polyurethane forms a shell portion and the (meth)acrylic resin forms a core portion, wherein the core-shell structure is formed by:
preparing an emulsion by emulsifying and dispersing the polyurethane and a (meth)acrylic monomer as a raw material for the (meth)acrylic resin in an aqueous medium, and
polymerizing the (meth)acrylic monomer, while the polyurethane undergoes a chain extension reaction, in the emulsion; and wherein a weight ratio of the polyurethane to the (meth) acrylic monomer is from 80/20 to 30/70, or (b) the urethane-(meth)acrylic composite resin according to (a), wherein the polyurethane constituting the composite resin is a polyurethane obtained from at least 2 polyol components and the polyvalent isocyanate component, and wherein polyol components each having a different number average molecular weight from each other and/or each comprising a different structural unit are used as the polyol components.

5. The aqueous dispersion of the urethane-(meth)acrylic composite resin according to claim 4, wherein a polyol unit(s) constituting the polyurethane has/have an average number of carbon atoms of from 2 to 4.

6. The aqueous dispersion of the urethane-(meth)acrylic composite resin according to claim 4, wherein the urethane-(meth)acrylic composite resin has a minimum film forming temperature of from −20 to 10° C.

7. The aqueous dispersion of the urethane-(meth)acrylic composite resin according to claim 4, wherein the polyurethane has an acid value of from 15 to 60 mg KOH/g.

8. The aqueous dispersion of the urethane-(meth)acrylic composite resin according to claim 4, wherein the polyurethane has a peak molecular weight (Mwp) of 30,000 or more and 200,000 or less.

9. The aqueous dispersion of the urethane-(meth)acrylic composite resin according to claim 4, wherein a polyol having the smallest number average molecular weight, of the plurality of polyols, has a number average molecular weight of 400 or more and 1,200 or less.

10. The aqueous dispersion of the urethane-(meth)acrylic composite resin according to claim 4, wherein a homopolymer or a copolymer composed of the (meth)acrylic monomer has a glass transition temperature (Tg) of 0° C. or more and 120° C. or less.

11. The aqueous dispersion of the urethane-(meth)acrylic composite resin according to claim 4, wherein the (meth) acrylic monomer is a mixture of a monomer whose homopolymer has a Tg of 95° C. or more, and a monomer whose homopolymer has a Tg of 30° C. or less.

12. The aqueous dispersion of the urethane-(meth)acrylic composite resin according to claim 4, wherein 100% or more of the carboxyl groups in the polyurethane are neutralized by a basic compound.

13. The urethane-(meth)acrylic composite resin according to claim 2, wherein the polyurethane constituting the composite resin is a polyurethane (component (A2)) obtained from the polyol component comprising the polyester polyol, and the polyvalent isocyanate component, and
wherein film formation by casting of a mixed solution of a silicone oil and the polyurethane (weight ratio 50/50), is possible at 23° C.

14. The urethane-(meth)acrylic composite resin according to claim 13, wherein the structural unit derived from the dicarboxylic acid in the polyester polyol, is a structural unit derived from isophthalic acid.

15. The urethane-(meth)acrylic composite resin according to claim 13, wherein the polyol component contains a dimethylolalkanoic acid.

16. The urethane-(meth)acrylic composite resin according to claim 15, wherein an alkane moiety of the dimethylolalkanoic acid has from 1 to 6 carbon atoms.

17. The urethane-(meth)acrylic composite resin according to claim 16, wherein the dimethylolalkanoic acid is dimethylolpropionic acid.

18. The urethane-(meth)acrylic composite resin according to claim 2, wherein film formation by casting of a mixed solution of a silicone oil and the urethane-(meth)acrylic composite resin prepared at a weight ratio of 50/50, is possible at 23° C.

19. The urethane-(meth)acrylic composite resin according to claim 2, wherein a content ratio of the polyurethane to the (meth)acrylic resin in the composite resin is within the range of from 80/20 to 30/70 in weight ratio, with a proviso that the total amount of both the components is 100.

20. An aqueous dispersion of a urethane-(meth)acrylic composite resin, obtained by emulsifying and dispersing the urethane-(meth)acrylic composite resin according to claim 2 in an aqueous medium.

21. A cosmetic comprising:
at least one urethane-(meth)acrylic composite resin selected from the group consisting of (i) and (ii), and having a weight average molecular weight (Mw) of one hundred thousand or more and two million or less, and a gel fraction of 20% by weight or more:
(i) an urethane-(meth)acrylic composite resin which is a composite resin obtained by complexing a polyurethane and a (meth)acrylic resin,
wherein the polyurethane is obtained from a polyol component comprising a polyester polyol, and a polyvalent isocyanate component;
wherein the polyester polyol comprises a structural unit derived from at least one dicarboxylic acid selected from the group consisting of phthalic acid, isophthalic acid and terephthalic acid; and
wherein a content percentage of the structural unit derived from the dicarboxylic acid is 0.05% by weight or more and 50% by weight or less; and
wherein the composite resin has a core-shell structure in which the polyurethane forms a shell portion and the (meth)acrylic resin forms a core portion,
wherein the core-shell structure is formed by:
preparing an emulsion by emulsifying and dispersing the polyurethane and a (meth)acrylic monomer as a raw material for the (meth)acrylic resin in an aqueous medium, and
polymerizing the (meth)acrylic monomer, while the polyurethane undergoes a chain extension reaction, in the emulsion,
and
(ii) the urethane-(meth)acrylic composite resin according to (i), wherein the polyurethane constituting the composite resin is a polyurethane (component (A2)) obtained from the polyol component comprising the polyester polyol, and the polyvalent isocyanate component, and
wherein film formation by casting of a mixed solution of a silicone oil and the polyurethane (weight ratio 50/50), is possible at 23° C., or
- at least one aqueous dispersion of the urethane-(meth)acrylic composite resin selected from the group consisting of (iii) and (iv), the composite resin having a gel fraction of 10% by weight or more:
  - (iii) an aqueous dispersion of a urethane-(meth)acrylic composite resin, obtained by dispersing an urethane-(meth)acrylic composite resin according to (a) or (b) in an aqueous medium:
    - (a) an urethane-(meth)acrylic composite resin which is a composite resin obtained by complexing a polyurethane and a (meth)acrylic resin,
    - wherein the polyurethane is obtained from a polyol component comprising a polyester polyol, and a polyvalent isocyanate component;
      - wherein the polyester polyol comprises a structural unit derived from at least one dicarboxylic acid selected from the group consisting of phthalic acid, isophthalic acid and terephthalic acid; and
      - wherein a content percentage of the structural unit derived from the dicarboxylic acid is 0.05% by weight or more and 50% by weight or less; and
    - wherein the composite resin has a core-shell structure in which the polyurethane forms a shell portion and the (meth)acrylic resin forms a core portion,
    - wherein the core-shell structure is formed by:
      - preparing an emulsion by emulsifying and dispersing the polyurethane and a (meth)acrylic monomer as a raw material for the (meth)acrylic resin in an aqueous medium, and
      - polymerizing the (meth)acrylic monomer, while the polyurethane undergoes a chain extension reaction, in the emulsion,
    - wherein a weight ratio of the polyurethane to the (meth)acrylic monomer is from 80/20 to 30/70, or
- (b) the urethane-(meth)acrylic composite resin according to (a), wherein the polyurethane constituting the composite resin is a polyurethane obtained from at least 2 polyol components and the polyvalent isocyanate component, and wherein the polyol components each having a different number average molecular weight from each other and/or each comprising a different structural unit are used as the polyol components, and
- (iv) an aqueous dispersion of a urethane-(meth)acrylic composite resin, obtained by emulsifying and dispersing the urethane-(meth)acrylic composite resin according to claim 2 in an aqueous medium.

22. A method for producing the urethane-(meth)acrylic composite resin according to claim 2,
- wherein a (meth) acrylate-based polymerizable monomer is subjected to emulsion polymerization in the presence of a polyurethane obtained from a polyol component comprising a polyester polyol, and a polyvalent isocyanate component.

\* \* \* \* \*